(12) United States Patent
Sonnenschein

(10) Patent No.: US 10,610,194 B2
(45) Date of Patent: Apr. 7, 2020

(54) DEVICE AND SYSTEM FOR MONITORING INTERNAL ORGANS OF A HUMAN OR ANIMAL

(71) Applicant: PULSENMORE LTD., Tel Aviv-Jaffa (IL)

(72) Inventor: Lazar Sonnenschein, Omer (IL)

(73) Assignee: Pulsenmore Ltd., Tel Aviv-Jaffa (IL)

( * ) Notice: Subject to any disclaimer, the term of this patent is extended or adjusted under 35 U.S.C. 154(b) by 426 days.

(21) Appl. No.: 15/538,511

(22) PCT Filed: Dec. 13, 2015

(86) PCT No.: PCT/IL2015/051209
§ 371 (c)(1),
(2) Date: Jun. 21, 2017

(87) PCT Pub. No.: WO2016/103250
PCT Pub. Date: Jun. 30, 2016

(65) Prior Publication Data
US 2018/0014811 A1 Jan. 18, 2018

(30) Foreign Application Priority Data
Dec. 25, 2014 (IL) .......................................... 236484

(51) Int. Cl.
*A61B 8/08* (2006.01)
*H04M 1/21* (2006.01)
*A61B 8/00* (2006.01)

(52) U.S. Cl.
CPC .............. *A61B 8/08* (2013.01); *A61B 8/0866* (2013.01); *A61B 8/4209* (2013.01);
(Continued)

(58) Field of Classification Search
CPC ......... A61B 8/08; A61B 8/0866; A61B 8/585; A61B 8/56; A61B 8/462; A61B 8/565;
(Continued)

(56) References Cited

U.S. PATENT DOCUMENTS 4,755,953 A * 7/1988 Geithman .............. G01N 29/11
702/39
7,549,961 B1  6/2009 Hwang
(Continued)

FOREIGN PATENT DOCUMENTS

CN  102098367  6/2011
CN  202362026  8/2012
(Continued)

OTHER PUBLICATIONS

Huang, Chih-Chung et al., "Implementation of a Smart-Phone Based Portable Doppler Flowmeter".(2011). IEEE International Ultrasonics Symposium, IUS. 1056-1059. 10.1109/ULTSYM.2011.0259. (4 pages).
(Continued)

*Primary Examiner* — Sanjay Cattungal
(74) *Attorney, Agent, or Firm* — Roach Brown McCarthy & Gruber, P.C.; Kevin D. McCarthy

(57) ABSTRACT

A hand-held system for ultrasound monitoring of internal organs of humans and animals and providing therapy combined with ultrasound is presented. The system comprises a base that functions as a docking station for the smart device. The base comprises ultrasound transducer elements, which are essentially integral with additional electronics, located on its bottom side and a socket into which the smart device can be inserted on its top side. The socket is provided with connecting elements suitable to mechanically and electrically connect the smart device to the base and to allow the base and the smart device to be moved as a single unit.

21 Claims, 13 Drawing Sheets

(52) U.S. Cl.
CPC .......... *A61B 8/4245* (2013.01); *A61B 8/4427* (2013.01); *A61B 8/4433* (2013.01); *A61B 8/4438* (2013.01); *A61B 8/4455* (2013.01); *A61B 8/4461* (2013.01); *A61B 8/4472* (2013.01); *A61B 8/462* (2013.01); *A61B 8/56* (2013.01); *A61B 8/565* (2013.01); *A61B 8/585* (2013.01); *H04M 1/21* (2013.01); *A61B 8/0808* (2013.01); *A61B 8/0883* (2013.01); *A61B 8/0891* (2013.01); *A61B 8/4466* (2013.01); *A61B 8/4488* (2013.01); *A61B 8/4494* (2013.01)

(58) Field of Classification Search
CPC ... A61B 8/4472; A61B 8/4461; A61B 8/4455; A61B 8/4438; A61B 8/4433; A61B 8/4427; A61B 8/4245; A61B 8/4209; A61B 8/0883; A61B 8/4466; A61B 8/0891; A61B 8/0808; A61B 8/4494; A61B 8/4488; H04M 1/21
See application file for complete search history.

(56) References Cited

U.S. PATENT DOCUMENTS

| | | | | |
|---|---|---|---|---|
| 9,327,142 | B2* | 5/2016 | Rothberg | A61B 8/145 |
| 9,980,700 | B2* | 5/2018 | Gubbini | A61B 8/4281 |
| 2009/0043204 | A1 | 2/2009 | Pelissier et al. | |
| 2011/0055447 | A1 | 3/2011 | Costa | |
| 2011/0237948 | A1 | 9/2011 | Corn | |
| 2012/0029303 | A1 | 2/2012 | Shaya | |
| 2012/0029358 | A1* | 2/2012 | Lin | A61B 8/0825 600/447 |
| 2012/0262221 | A1* | 10/2012 | Bottarel | B06B 1/0215 327/434 |
| 2013/0265100 | A1* | 10/2013 | Bottarel | H03K 17/08104 327/434 |
| 2014/0024939 | A1 | 1/2014 | Kato et al. | |
| 2014/0236011 | A1* | 8/2014 | Fan | A61B 5/6876 600/440 |
| 2014/0243669 | A1 | 8/2014 | Halmann et al. | |
| 2014/0355381 | A1* | 12/2014 | Lal | B81B 3/0021 367/87 |
| 2015/0018679 | A1* | 1/2015 | Endo | A61B 8/485 600/438 |
| 2016/0061650 | A1* | 3/2016 | Sato | A61B 5/0095 73/655 |
| 2016/0302766 | A1* | 10/2016 | Liu | A61B 8/4236 |

FOREIGN PATENT DOCUMENTS

| | | |
|---|---|---|
| JP | 11290321 A | 10/1999 |
| JP | 2003033350 | 2/2003 |
| JP | 2013085688 | 5/2013 |
| JP | 2014150936 | 8/2014 |
| KR | 20140143125 | 12/2014 |
| WO | 2014/041503 | 3/2014 |
| WO | 2014/077606 | 5/2014 |

OTHER PUBLICATIONS

Communication and Supplemental European Search Report for a counterpart foreign application—EP 15 87 2093; dated Aug. 9, 2018 (13 pages).
Japanese Patent Office's office action for a counterpart foreign application—JP 2017-534740; dated Jul. 30, 2019 (4 pages) and English translation (3 pages).
International Search Report for PCT/IL2015/051209, dated Mar. 29, 2016, 5 pages.
Written Opinion of the International Searching Authority for PCT/IL2015/051209, dated Mar. 29, 2016, 7 pages.
International Preliminary Report on Patentability for PCT/IL2015/051209, dated May 4, 2017, 16 page.

* cited by examiner

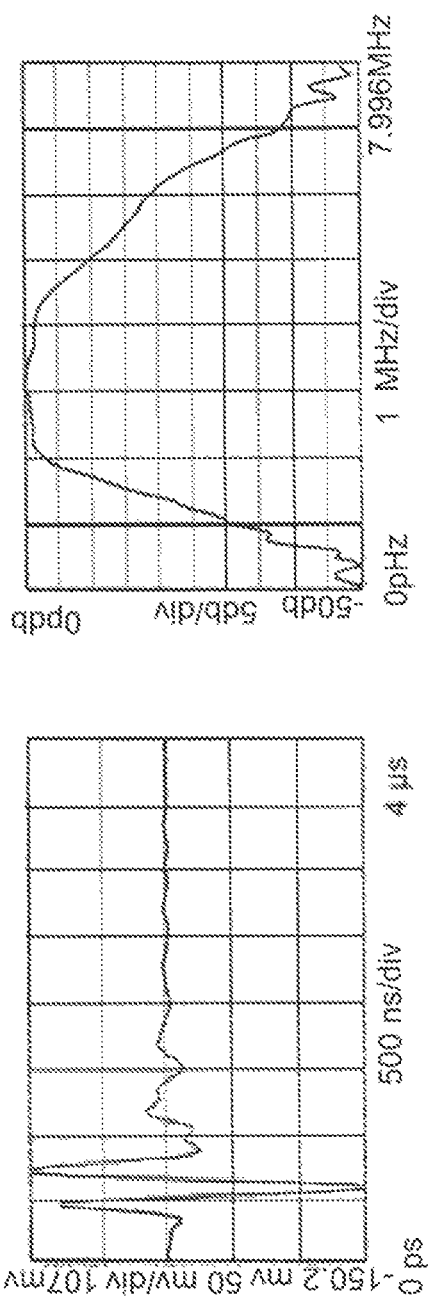
Fig. 11A
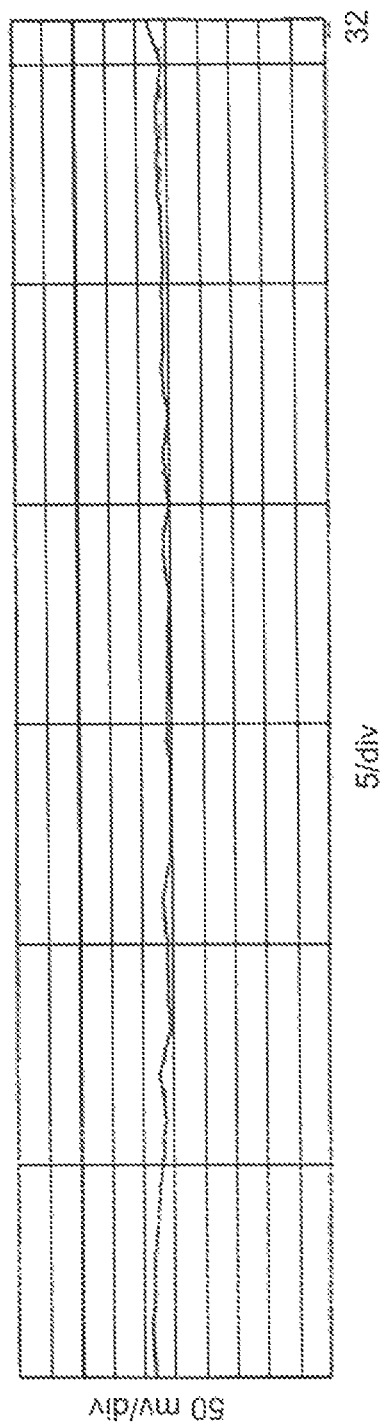
Fig. 11B
Fig. 11C

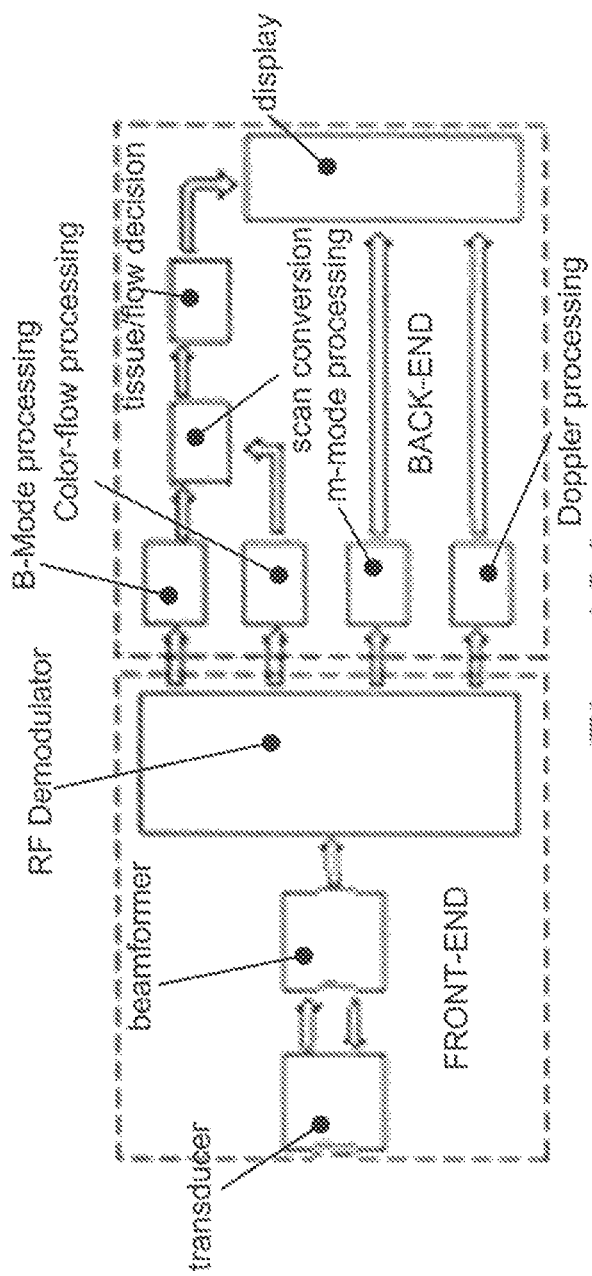
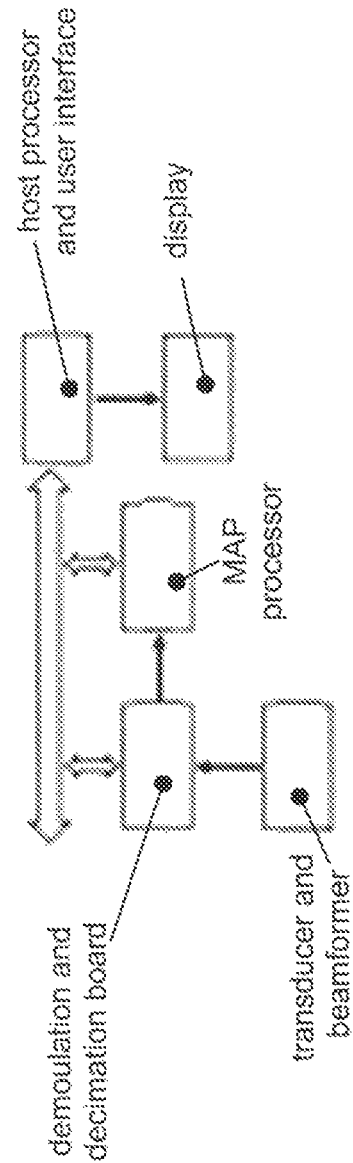

DEVICE AND SYSTEM FOR MONITORING INTERNAL ORGANS OF A HUMAN OR ANIMAL

FIELD OF THE INVENTION

The present invention relates to the field of medical devices. In particular, the invention relates to the field of devices and systems for monitoring of internal organs of humans and animals and therapy combined with ultrasound.

BACKGROUND OF THE INVENTION

In order to demonstrate the invention, a specific example, will be presented from the field of obstetrics. The problem of fetus welfare during pregnancy is a widespread one, particularly during advanced pregnancy months when the mother already senses fetal movements. The prolonged absence of fetal movement may be the harbinger of serious problems, or may simply be the result of a naturally reduced fetal activity. However, as the concern arise at all times of day it is not always possible for the mother to consult with a healthcare specialist. Accordingly, pregnant women often take unnecessary trips to the emergency room of the nearest hospital, or get their physician to make a call, to verify that nothing is wrong with the fetus or use artificial means to increase fetal movement. Moreover, women with diabetes or older than 40 years (for example) are considered in many cases to be pregnant women at risk and therefore are instructed to remain in bed, or at the very least to stay at home with limited activity, if alarming signs exist that a miscarriage could occur as a result of excessive activity. Women in such conditions need closer monitoring of fetal activity so as to be warned in time if any negative development appears to be taking place.

In most cases, not feeling the movements of the fetus does not mean that anything is wrong with it, and after much tension and hassle, the mother is reassured. An immediate way of making sure that the fetus is moving is by using ultrasound apparatus, which is available in most if not all clinical facilities. However, such apparatus is sophisticated and expensive, in the order of several thousand dollars and more. Accordingly, some companies attempted to sell less-expensive versions of such ultrasound apparatus, but the result was still prohibitively costly, such that very few households can afford it, particularly taking into account that such apparatus is only needed for a few months.

Simple Doppler devices based on single element, which only provide as output the sound of fetal pulse, are reasonably priced in the USD 100-200 range, but do not provide a sufficient level of information on the actual fetal status, since they cannot offer any indication of fetus movement and they cannot generate images of the fetus.

It is therefore clear that it would be highly desirable to provide an affordable solution that will permit future mothers to visually monitor their future baby's activity, thus preventing the anxiety, cost and hassle associated with the above-mentioned problem.

In addition, it might be useful to measure some other parameters, hence providing more information for decision makers regarding the patient's status. These other parameters can be used to determine for example, the fetal presentation, the date of the pregnancy (gestational age), to confirm fetal viability, to determine location of fetus, intra-uterine vs ectopic, to check the location of the placenta in relation to the cervix, for amniotic fluid evaluation, to check for the number of fetuses (multiple pregnancy), to check for major physical abnormalities, to assess fetal growth (for evidence of intrauterine growth restriction (IUGR)) and to check for fetal movement and heartbeat, i.e. fetal cardiac activity.

It is an object of the present invention to provide such a low cost solution, which overcomes the drawbacks of the prior art.

Another object of the present invention is to provide a low cost solution that enables the physician to monitor the pregnant patient at home, from his office.

Operating ultrasound clinical apparatus requires expertise. Accordingly, it is another object of the invention to provide a solution that can be easily operated by a person who is not a healthcare specialist.

Other objects and advantages of the invention will be appreciated through the following illustrative and non-limitative description of embodiments of the invention.

SUMMARY OF THE INVENTION

In a first aspect the invention is a base for an ultrasonic system, the base comprising connection elements, adapted to mechanically and electrically connect a smart device to the base and to allow the base and the smart device to be moved as a single unit and an ultrasonic array with at least one element capable of generating a signal in the range of 1 MHz to 15 MHz.

In embodiments of the base of the first aspect of the invention the connection elements comprise a cavity adapted to accept and position the smart device. Embodiments of the base of the first aspect of the invention comprise electronics adapted to operate the ultrasonic array and to convey a signal generated thereby to storage elements. The storage elements are provided in at least one of: the smart device; the base; and a location remote from the base.

In embodiments of the base of the first aspect of the invention electrical power to activate the ultrasonic array is supplied from one of: a rechargeable battery and a DC to DC converter located in the base; a rechargeable battery and a switching power supply, comprised of a power stage and a control circuit, located in the base; and a battery in the smart device. In embodiments of the base of the first aspect of the invention some or all of the electronics are located in at least one of: the base; the smart device; and on a semiconductor layer produced integrally with the elements that produce ultrasound waves using wafer technology.

In embodiments of the base of the first aspect of the invention the elements that produce ultrasound waves are one of: Capacitive Micromachined Ultrasonic Transducers (CMUT), Piezoelectric Micromachined Ultrasonic Transducers (PMUT), Piezo composite Transducers or bulk Piezo elements Transducers.

Embodiments of the base of the first aspect of the invention comprise software adapted to enable operation of the ultrasonic array and to display the results of the operation as visible images.

In a second embodiment the invention is a base for an ultrasonic system, the base comprising connection elements, adapted to mechanically and electrically connect a smart device to the base and to allow the base and the smart device to be moved as a single unit and an ultrasonic array having the following configuration: a 1D linear array that produces a straight beam that focuses in one axis at different depths and angles and whose divergence increases with angle and depth.

In embodiments of the base of the second aspect of the invention the connection elements comprise a cavity adapted to accept and position the smart device. Embodiments of the base of the second aspect of the invention comprise electronics adapted to operate the ultrasonic array and to convey a signal generated thereby to storage elements. The storage elements are provided in at least one of: the smart device; the base; and a location remote from the base.

In embodiments of the base of the second aspect of the invention electrical power to activate the ultrasonic array is supplied from one of: a rechargeable battery and a DC to DC converter located in the base; a rechargeable battery and a switching power supply, comprised of a power stage and a control circuit, located in the base; and a battery in the smart device. In embodiments of the base of the second aspect of the invention some or all of the electronics are located in at least one of: the base; the smart device; and on a semiconductor layer produced integrally with the elements that produce ultrasound waves using wafer technology.

In embodiments of the base of the second aspect of the invention the elements that produce ultrasound waves are one of: Capacitive Micromachined Ultrasonic Transducers (CMUT), Piezoelectric Micromachined Ultrasonic Transducers (PMUT), Piezo composite Transducers or bulk Piezo elements Transducers.

Embodiments of the base of the second aspect of the invention comprise software adapted to enable operation of the ultrasonic array and to display the results of the operation as visible images.

In a third aspect the invention is a base for an ultrasonic system, the base comprising connection elements, adapted to mechanically and electrically connect a smart device to the base and to allow the base and the smart device to be moved as a single unit and an ultrasonic array having the following configuration: a 2D square array that has steering capability in three dimensions with spherical or single-axis focus.

In embodiments of the base of the third aspect of the invention the connection elements comprise a cavity adapted to accept and position the smart device. Embodiments of the base of the third aspect of the invention are adapted to operate the ultrasonic array and to convey a signal generated thereby to storage elements. The storage elements are provided in at least one of: the smart device; the base; and a location remote from the base.

In embodiments of the base of the third aspect of the invention electrical power to activate the ultrasonic array is supplied from one of: a rechargeable battery and a DC to DC converter located in the base; a rechargeable battery and a switching power supply, comprised of a power stage and a control circuit, located in the base; and a battery in the smart device. In embodiments of the base of the third aspect of the invention some or all of the electronics are located in at least one of: the base; the smart device; and on a semiconductor layer produced integrally with the elements that produce ultrasound waves using wafer technology.

In embodiments of the base of the third aspect of the invention the elements that produce ultrasound waves are one of: Capacitive Micromachined Ultrasonic Transducers (CMUT), Piezoelectric Micromachined Ultrasonic Transducers (PMUT), Piezo composite Transducers or bulk Piezo elements Transducers.

Embodiments of the base of the third aspect of the invention comprise software adapted to enable operation of the ultrasonic array and to display the results of the operation as visible images.

In a fourth aspect the invention is a base for an ultrasonic system, the base comprising connection elements, adapted to mechanically and electrically connect a smart device to the base and to allow the base and the smart device to be moved as a single unit and an ultrasonic array having the following configuration: a 1.5D square or rectangular matrix array that has steering capability and focuses on one axis at different depths and angles.

In embodiments of the base of the fourth aspect of the invention the connection elements comprise a cavity adapted to accept and position the smart device. Embodiments of the base of the fourth aspect of the invention comprise electronics adapted to operate the ultrasonic array and to convey a signal generated thereby to storage elements. The storage elements are provided in at least one of: the smart device; the base; and a location remote from the base.

In embodiments of the base of the fourth aspect of the invention electrical power to activate the ultrasonic array is supplied from one of: a rechargeable battery and a DC to DC converter located in the base; a rechargeable battery and a switching power supply, comprised of a power stage and a control circuit, located in the base; and a battery in the smart device. In embodiments of the base of the fourth aspect of the invention some or all of the electronics are located in at least one of: the base; the smart device; and on a semiconductor layer produced integrally with the elements that produce ultrasound waves using wafer technology.

In embodiments of the base of the fourth aspect of the invention the elements that produce ultrasound waves are one of: Capacitive Micromachined Ultrasonic Transducers (CMUT), Piezoelectric Micromachined Ultrasonic Transducers (PMUT), Piezo composite Transducers or bulk Piezo elements Transducers.

Embodiments of the base of the fourth aspect of the invention comprise software adapted to enable operation of the ultrasonic array and to display the results of the operation as visible images.

In a fifth aspect the invention is a base for an ultrasonic system, the base comprising connection elements, adapted to mechanically and electrically connect a smart device to the base and to allow the base and the smart device to be moved as a single unit and an ultrasonic array having the following configuration: a 1D annular array that has spherical focusing at different depths.

In embodiments of the base of the fifth aspect of the invention the connection elements comprise a cavity adapted to accept and position the smart device. Embodiments of the base of the fifth aspect of the invention comprise electronics adapted to operate the ultrasonic array and to convey a signal generated thereby to storage elements. In embodiments of the base of the fifth aspect of the invention the storage elements are provided in at least one of: the smart device; the base; and a location remote from the base.

In embodiments of the base of the fifth aspect of the invention electrical power to activate the ultrasonic array is supplied from one of: a rechargeable battery and a DC to DC converter located in the base; a rechargeable battery and a switching power supply, comprised of a power stage and a control circuit, located in the base; and a battery in the smart device. In embodiments of the base of the fifth aspect of the invention some or all of the electronics are located in at least one of: the base; the smart device; and on a semiconductor layer produced integrally with the elements that produce ultrasound waves using wafer technology.

In embodiments of the base of the fifth aspect of the invention the elements that produce ultrasound waves are one of: Capacitive Micromachined Ultrasonic Transducers (CMUT), Piezoelectric Micromachined Ultrasonic Transducers (PMUT), Piezo composite Transducers or bulk Piezo elements Transducers.

Embodiments of the base of the fifth aspect of the invention comprise software adapted to enable operation of the ultrasonic array and to display the results of the operation as visible images.

In a sixth aspect the invention is a base for an ultrasonic system, the base comprising connection elements, adapted to mechanically and electrically connect a smart device to the base and to allow the base and the smart device to be moved as a single unit and an ultrasonic array having the following configuration: a 2D segmented annular array that produces an elliptical or spherical beam with steering capability at different depths and angles.

In embodiments of the base of the sixth aspect of the invention the connection elements comprise a cavity adapted to accept and position the smart device. Embodiments of the base of the sixth aspect of the invention comprise electronics adapted to operate the ultrasonic array and to convey a signal generated thereby to storage elements. The storage elements are provided in at least one of: the smart device; the base; and a location remote from the base.

In embodiments of the base of the sixth aspect of the invention electrical power to activate the ultrasonic array is supplied from one of: a rechargeable battery and a DC to DC converter located in the base; a rechargeable battery and a switching power supply, comprised of a power stage and a control circuit, located in the base; and a battery in the smart device. In embodiments of the base of the sixth aspect of the invention some or all of the electronics are located in at least one of: the base; the smart device; and on a semiconductor layer produced integrally with the elements that produce ultrasound waves using wafer technology.

In embodiments of the base of the sixth aspect of the invention the elements that produce ultrasound waves are one of: Capacitive Micromachined Ultrasonic Transducers (CMUT), Piezoelectric Micromachined Ultrasonic Transducers (PMUT), Piezo composite Transducers or bulk Piezo elements Transducers.

Embodiments of the base of the sixth aspect of the invention comprise software adapted to enable operation of the ultrasonic array and to display the results of the operation as visible images.

In a seventh aspect the invention is a base for an ultrasonic system, the base comprising connection elements, adapted to mechanically and electrically connect a smart device to the base and to allow the base and the smart device to be moved as a single unit and an ultrasonic array having the following configuration: a 1D circular array that produces an elliptical or spherical beam with steering capabilities.

In embodiments of the base of the seventh aspect of the invention the connection elements comprise a cavity adapted to accept and position the smart device. Embodiments of the base of the seventh aspect of the invention comprise electronics adapted to operate the ultrasonic array and to convey a signal generated thereby to storage elements. In embodiments of the base of the seventh aspect of the invention the storage elements are provided in at least one of: the smart device; the base; and a location remote from the base.

In embodiments of the base of the seventh aspect of the invention electrical power to activate the ultrasonic array is supplied from one of: a battery and a DC to DC converter located in the base; a battery and a switching power supply, comprised of a power stage and a control circuit, located in the base; and a battery in the smart device. In embodiments of the base of the seventh aspect of the invention some or all of the electronics are located in at least one of: the base; the smart device; and on a semiconductor layer produced integrally with the elements that produce ultrasound waves using wafer technology.

In embodiments of the base of the seventh aspect of the invention the elements that produce ultrasound waves are one of: Capacitive Micromachined Ultrasonic Transducers (CMUT), Piezoelectric Micromachined Ultrasonic Transducers (PMUT), Piezo composite Transducers or bulk Piezo elements Transducers.

Embodiments of the base of the seventh aspect of the invention comprise software adapted to enable operation of the ultrasonic array and to display the results of the operation as visible images.

In an eighth aspect the invention is a system for ultrasonic imaging comprising: a base; a smart device; an ultrasonic array; electronics adapted to operate the ultrasonic array and to convey a signal generated thereby to storage elements; and software adapted to enable operation of the ultrasonic array, to receive signals relating to ultrasonic images, to perform desired operations on the signals and to display the results of the operations as visible images; wherein the base comprises connection elements, adapted to mechanically and electrically connect the smart device to the base and to allow the base and the smart device to be moved as a single unit and the ultrasonic array comprises at least one element capable of generating a signal in the range of 1 MHz to 15 MHz.

In embodiments of the system of the eighth aspect of the invention data integrity, encryption, and other data activities can be supported from a mobile network operator's servers or a cloud.

In embodiments of the system of the eighth aspect of the invention all digital and analog components of an ultrasound system are located on the base. In embodiments of the system of the eighth aspect of the invention all digital and analog components of an ultrasound system are implemented in existing chips on the smart device.

In embodiments of the system of the eighth aspect of the invention at least a part of the software adapted to receive signals relating to ultrasonic images and to perform desired operations thereon is located on at least one of: the base and the smart device. In embodiments of the system of the eighth aspect of the invention the smart device comprises dedicated software in the form of an application that is downloaded from one of: the internet, a cloud, or from the base.

Embodiments of the system of the eighth aspect of the invention comprise communication components allowing at least one of: two-way communication between the base and the smart device and two-way communication between the system and an external location. In embodiments of the system of the eighth aspect of the invention at least a part of the communication components are located on at least one of: the base and the smart device. In embodiments of the system of the eighth aspect of the invention the base has an internal code (characters and numbers) that provides its unique identification; thereby allowing secured communication with remote locations. In embodiments of the system of the eighth aspect of the invention the secured communication allows a physician to take over the control of the application in the smart device and record, send images or video from the system to his computer, to the cloud or to any other desired location. In embodiments of the system of the eighth aspect of the invention the secured communication allows a patient using the system to send images or video to a medical center or to a physician.

In a ninth aspect the invention is a system for ultrasonic imaging comprising: a base; a smart device; an ultrasonic array; electronics adapted to operate the ultrasonic array and to convey a signal generated thereby to storage elements; and software adapted to enable operation of the ultrasonic array, to receive signals relating to ultrasonic images, to perform desired operations on the signals and to display the results of the operations as visible images; wherein the base comprises connection elements, adapted to mechanically and electrically connect the smart device to the base and to allow the base and the smart device to be moved as a single unit and the ultrasonic array comprises a 1D linear array that produces a straight beam that focuses in one axis at different depths and angles and whose divergence increases with angle and depth.

In embodiments of the system of the ninth aspect of the invention data integrity, encryption, and other data activities can be supported from a mobile network operator's servers or a cloud.

In embodiments of the system of the ninth aspect of the invention all digital and analog components of an ultrasound system are located on the base. In embodiments of the system of the ninth aspect of the invention all digital and analog components of an ultrasound system are implemented in existing chips on the smart device.

In embodiments of the system of the ninth aspect of the invention at least a part of the software adapted to receive signals relating to ultrasonic images and to perform desired operations thereon is located on at least one of: the base and the smart device. In embodiments of the system of the ninth aspect of the invention the smart device comprises dedicated software in the form of an application that is downloaded from one of: the internet, a cloud, or from the base.

Embodiments of the system of the ninth aspect of the invention comprise communication components allowing at least one of: two-way communication between the base and the smart device and two-way communication between the system and an external location. In embodiments of the system of the ninth aspect of the invention at least a part of the communication components are located on at least one of: the base and the smart device. In embodiments of the system of the ninth aspect of the invention the base has an internal code (characters and numbers) that provides its unique identification; thereby allowing secured communication with remote locations. In embodiments of the system of the ninth aspect of the invention the secured communication allows a physician to take over the control of the application in the smart device and record, send images or video from the system to his computer, to the cloud or to any other desired location. In embodiments of the system of the ninth aspect of the invention the secured communication allows a patient using the system to send images or video to a medical center or to a physician.

In a tenth aspect the invention is a system for ultrasonic imaging comprising: a base; a smart device; an ultrasonic array; electronics adapted to operate the ultrasonic array and to convey a signal generated thereby to storage elements; and software adapted to enable operation of the ultrasonic array, to receive signals relating to ultrasonic images, to perform desired operations on the signals and to display the results of the operations as visible images; wherein the base comprises connection elements, adapted to mechanically and electrically connect the smart device to the base and to allow the base and the smart device to be moved as a single unit and the ultrasonic array comprises a 2D square array that has steering capability in three dimensions with spherical or single-axis focus.

In embodiments of the system of the tenth aspect of the invention data integrity, encryption, and other data activities can be supported from a mobile network operator's servers or a cloud.

In embodiments of the system of the tenth aspect of the invention all digital and analog components of an ultrasound system are located on the base. In embodiments of the system of the tenth aspect of the invention all digital and analog components of an ultrasound system are implemented in existing chips on the smart device.

In embodiments of the system of the tenth aspect of the invention at least a part of the software adapted to receive signals relating to ultrasonic images and to perform desired operations thereon is located on at least one of: the base and the smart device. In embodiments of the system of the tenth aspect of the invention the smart device comprises dedicated software in the form of an application that is downloaded from one of: the internet, a cloud, or from the base.

Embodiments of the system of the tenth aspect of the invention comprise communication components allowing at least one of: two-way communication between the base and the smart device and two-way communication between the system and an external location. In embodiments of the system of the tenth aspect of the invention at least a part of the communication components are located on at least one of: the base and the smart device. In embodiments of the system of the tenth aspect of the invention the base has an internal code (characters and numbers) that provides its unique identification; thereby allowing secured communication with remote locations. In embodiments of the system of the tenth aspect of the invention the secured communication allows a physician to take over the control of the application in the smart device and record, send images or video from the system to his computer, to the cloud or to any other desired location. In embodiments of the system of the tenth aspect of the invention the secured communication allows a patient using the system to send images or video to a medical center or to a physician.

In an eleventh aspect the invention is a system for ultrasonic imaging comprising: a base; a smart device; an ultrasonic array; electronics adapted to operate the ultrasonic array and to convey a signal generated thereby to storage elements; and software adapted to enable operation of the ultrasonic array, to receive signals relating to ultrasonic images, to perform desired operations on the signals and to display the results of the operations as visible images; wherein the base comprises connection elements, adapted to mechanically and electrically connect the smart device to the base and to allow the base and the smart device to be moved as a single unit and the ultrasonic array comprises a 1.5D square or rectangular matrix array that has steering capability and focuses on one axis at different depths and angles.

In embodiments of the system of the eleventh aspect of the invention data integrity, encryption, and other data activities can be supported from a mobile network operator's servers or a cloud.

In embodiments of the system of the eleventh aspect of the invention all digital and analog components of an ultrasound system are located on the base. In embodiments of the system of the eleventh aspect of the invention all digital and analog components of an ultrasound system are implemented in existing chips on the smart device.

In embodiments of the system of the eleventh aspect of the invention at least a part of the software adapted to receive signals relating to ultrasonic images and to perform desired operations thereon is located on at least one of: the base and the smart device. In embodiments of the system of the eleventh aspect of the invention the smart device comprises dedicated software in the form of an application that is downloaded from one of: the internet, a cloud, or from the base.

Embodiments of the system of the eleventh aspect of the invention comprise communication components allowing at least one of: two-way communication between the base and the smart device and two-way communication between the system and an external location. In embodiments of the system of the eleventh aspect of the invention at least a part of the communication components are located on at least one of: the base and the smart device. In embodiments of the system of the eleventh aspect of the invention the base has an internal code (characters and numbers) that provides its unique identification; thereby allowing secured communication with remote locations. In embodiments of the system of the eleventh aspect of the invention the secured communication allows a physician to take over the control of the application in the smart device and record, send images or video from the system to his computer, to the cloud or to any other desired location. In embodiments of the system of the eleventh aspect of the invention the secured communication allows a patient using the system to send images or video to a medical center or to a physician.

In a twelfth aspect the invention is a system for ultrasonic imaging comprising: a base; a smart device; an ultrasonic array; electronics adapted to operate the ultrasonic array and to convey a signal generated thereby to storage elements; and software adapted to enable operation of the ultrasonic array, to receive signals relating to ultrasonic images, to perform desired operations on the signals and to display the results of the operations as visible images; wherein the base comprises connection elements, adapted to mechanically and electrically connect the smart device to the base and to allow the base and the smart device to be moved as a single unit and the ultrasonic array comprises a 1D annular array that has spherical focusing at different depths.

In embodiments of the system of the twelfth aspect of the invention data integrity, encryption, and other data activities can be supported from a mobile network operator's servers or a cloud.

In embodiments of the system of the twelfth aspect of the invention all digital and analog components of an ultrasound system are located on the base. In embodiments of the system of the twelfth aspect of the invention all digital and analog components of an ultrasound system are implemented in existing chips on the smart device.

In embodiments of the system of the twelfth aspect of the invention at least a part of the software adapted to receive signals relating to ultrasonic images and to perform desired operations thereon is located on at least one of: the base and the smart device. In embodiments of the system of the twelfth aspect of the invention the smart device comprises dedicated software in the form of an application that is downloaded from one of: the internet, a cloud, or from the base.

Embodiments of the system of the twelfth aspect of the invention comprise communication components allowing at least one of: two-way communication between the base and the smart device and two-way communication between the system and an external location. In embodiments of the system of the twelfth aspect of the invention at least a part of the communication components are located on at least one of: the base and the smart device. In embodiments of the system of the twelfth aspect of the invention the base has an internal code (characters and numbers) that provides its unique identification; thereby allowing secured communication with remote locations. In embodiments of the system of the twelfth aspect of the invention the secured communication allows a physician to take over the control of the application in the smart device and record, send images or video from the system to his computer, to the cloud or to any other desired location. In embodiments of the system of the twelfth aspect of the invention the secured communication allows a patient using the system to send images or video to a medical center or to a physician.

In a thirteenth aspect the invention is a system for ultrasonic imaging comprising: a base; a smart device; an ultrasonic array; electronics adapted to operate the ultrasonic array and to convey a signal generated thereby to storage elements; and software adapted to enable operation of the ultrasonic array, to receive signals relating to ultrasonic images, to perform desired operations on the signals and to display the results of the operations as visible images; wherein the base comprises connection elements, adapted to mechanically and electrically connect the smart device to the base and to allow the base and the smart device to be moved as a single unit and the ultrasonic array is a 2D segmented annular array that produces an elliptical or spherical beam with steering capability at different depths and angles.

In embodiments of the system of the thirteenth aspect of the invention data integrity, encryption, and other data activities can be supported from a mobile network operator's servers or a cloud.

In embodiments of the system of the thirteenth aspect of the invention all digital and analog components of an ultrasound system are located on the base. In embodiments of the system of the thirteenth aspect of the invention all digital and analog components of an ultrasound system are implemented in existing chips on the smart device.

In embodiments of the system of the thirteenth aspect of the invention at least a part of the software adapted to receive signals relating to ultrasonic images and to perform desired operations thereon is located on at least one of: the base and the smart device. In embodiments of the system of the thirteenth aspect of the invention the smart device comprises dedicated software in the form of an application that is downloaded from one of: the internet, a cloud, or from the base.

Embodiments of the system of the thirteenth aspect of the invention comprise communication components allowing at least one of: two-way communication between the base and the smart device and two-way communication between the system and an external location. In embodiments of the system of the thirteenth aspect of the invention at least a part of the communication components are located on at least one of: the base and the smart device. In embodiments of the system of the thirteenth aspect of the invention the base has an internal code (characters and numbers) that provides its unique identification; thereby allowing secured communication with remote locations. In embodiments of the system of the thirteenth aspect of the invention the secured communication allows a physician to take over the control of the application in the smart device and record, send images or video from the system to his computer, to the cloud or to any other desired location. In embodiments of the system of the thirteenth aspect of the invention the secured communication allows a patient using the system to send images or video to a medical center or to a physician.

In a fourteenth aspect the invention is a system for ultrasonic imaging comprising: a base; a smart device; an ultrasonic array; electronics adapted to operate the ultrasonic array and to convey a signal generated thereby to storage elements; and software adapted to enable operation of the ultrasonic array, to receive signals relating to ultrasonic images, to perform desired operations on the signals and to display the results of the operations as visible images; wherein the base comprises connection elements, adapted to mechanically and electrically connect the smart device to the base and to allow the base and the smart device to be moved as a single unit and the ultrasonic array comprises a 1D circular array that produces an elliptical or spherical beam with steering capabilities.

In embodiments of the system of the fourteenth aspect of the invention data integrity, encryption, and other data activities can be supported from a mobile network operator's servers or a cloud.

In embodiments of the system of the fourteenth aspect of the invention digital and analog components of an ultrasound system are located on the base. In embodiments of the system of the fourteenth aspect of the invention all digital and analog components of an ultrasound system are implemented in existing chips on the smart device.

In embodiments of the system of the fourteenth aspect of the invention at least a part of the software adapted to receive signals relating to ultrasonic images and to perform desired operations thereon is located on at least one of: the base and the smart device. In embodiments of the system of the fourteenth aspect of the invention the smart device comprises dedicated software in the form of an application that is downloaded from one of: the internet, a cloud, or from the base.

Embodiments of the system of the fourteenth aspect of the invention comprise communication components allowing at least one of: two-way communication between the base and the smart device and two-way communication between the system and an external location. In embodiments of the system of the fourteenth aspect of the invention at least a part of the communication components are located on at least one of: the base and the smart device. In embodiments of the system of the fourteenth aspect of the invention the base has an internal code (characters and numbers) that provides its unique identification; thereby allowing secured communication with remote locations. In embodiments of the system of the fourteenth aspect of the invention the secured communication allows a physician to take over the control of the application in the smart device and record, send images or video from the system to his computer, to the cloud or to any other desired location. In embodiments of the system of the fourteenth aspect of the invention the secured communication allows a patient using the system to send images or video to a medical center or to a physician.

BRIEF DESCRIPTION OF THE DRAWINGS

In the drawings:

FIG. 11A and FIG. 11B are graphs showing respectively the time and frequency responses for one element out of the 32 elements in a prototype transducer;

FIG. 11 C is a graph showing the variation in sensitivity for the elements in the 32 element prototype transducer;

DETAILED DESCRIPTION OF THE INVENTION

Figure 1:
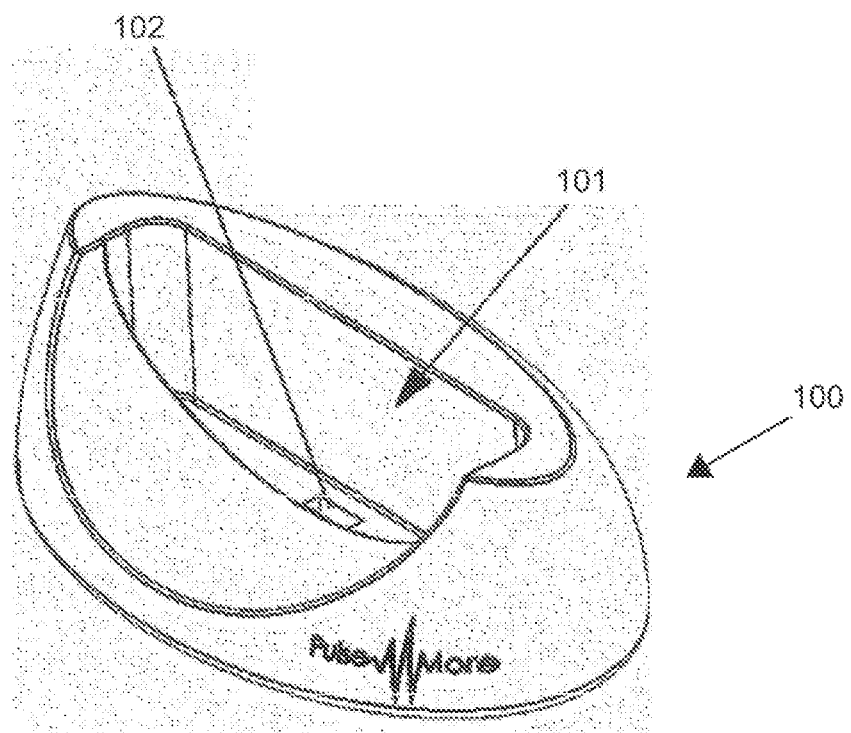
FIG. 1 is a schematic perspective view of a base for the system according to one embodiment of the invention.

The invention is based on a novel combination of a new architecture of an ultrasound elements assembly, with software operated via any suitable personal communication device.

Suitable personal communication devices include, for example, a commercially-available smart phone, or mobile devices such as an IPOD, MP4 or Android devices with wireless communication capabilities such as WI-FI or LTE. Of course, personal communication devices are developed constantly and any suitable device that will be developed in the future will be useful in the context of the invention, which is not limited to any specific connectable device. For the sake of brevity, all the suitable devices will be referred to hereinafter cumulatively as "smart device".

The system of the invention comprises a base that functions as a docking station for the smart device. The base is provided with connecting elements suitable to connect it to the smart device. The base comprises a socket into which the smart device can be inserted on its top side and ultrasound transducer elements located on its bottom side, which are essentially integral with additional electronics, as will be more fully described herein below.

The architecture of the ultrasound assembly makes it possible to produce systems comprising a base and smart device according to the invention, which are affordable by any person. The inventors estimate that the base, including the ultrasound elements assembly would cost in the range of a few tens of dollars. The smart device of the system of the invention is a standard one that is owned by most persons and only requires in some embodiments the addition of dedicated software, e.g. via an application that can be downloaded from the internet, a cloud or from the base, to be able to carry out the invention as described herein below.

As said, the invention is not limited to any specific smart device. For instance, the invention will be operable with devices using more advanced generations such 4G, 4.5G, 5G, 6G or other cellular communication capabilities. The important factor is that any device that will be employed instead of the exemplified iPhone (which is only provided as an example of one of the many suitable smart devices) should not require modification by the addition of specialized hardware and should not require skilled personnel to be operated but can be used by every consumer.

Throughout this description when reference is made to a "smart device" or to a "smart phone" as an example of a smart device, it should be interpreted in the broadest way to include each and every device that has the capacity to receive an input, to run software and, optionally, is provided with communication capabilities, such as Wi-Fi, LTE, S-UMTS, HSPA+, advanced wireless communication, wired communication, mobile communication generation such as 4G, 4.5G. 5G, 6G, Bluetooth, cellular networks, and with any communication protocol that connects two independent devices.

While the invention will be illustrated with particular reference to fetal monitoring, it is by no means limited to such uses. In a similar way, however with different ultrasound devices, the same principles of the invention can be used to measure and evaluate other medical conditions, e.g. the liver, cardiovascular system and abnormalities. Additional illustrative uses are, for instance:

A. Doppler of the carotid, which shows whether a waxy substance called plaque has built up in the carotid arteries. The buildup of plaque in the carotid arteries is called carotid artery disease. A carotid artery duplex scan is a type of vascular ultrasound study done to assess the blood flow of the arteries that supply blood from the heart through the neck to the brain. There are 2 carotid arteries, each of which divides into two more: the right internal and external carotid arteries and the left internal and external carotid arteries. The vertebrobasilar artery system, which is the other major blood vessel that supplies the brain, may be studied as well.

The term "duplex" refers to the fact that two modes of ultrasound are used—Doppler and B-mode. The B-mode transducer obtains an image of the carotid artery being studied. The Doppler probe within the transducer evaluates the velocity and direction of blood flow in the vessel. The probe (also called a transducer) sends out ultrasonic sound waves at a high frequency. When the probe is placed on the carotid arteries at certain locations and angles, the ultrasonic sound waves move through the skin and other body tissues to the blood vessels, where the waves echo off of the blood cells. The transducer picks up the reflected waves and sends them to an amplifier, which makes the ultrasonic sound waves audible. Absence or faintness of these sounds may indicate an obstruction to the blood flow.

B. Veins or arteries: Lower extremity venous ultrasound is typically performed if a clot in the vein (deep venous thrombosis or DVT) is suspected. The veins in the legs are compressed and the blood flow is assessed to make sure the vein is not clogged. This test is also used to look for chronic venous insufficiency, or leaky valves in the veins which may cause swelling or edema.

Lower extremity arterial ultrasound may be performed in patients with peripheral arterial disease (PAD), particularly for planning an endovascular procedure or surgery. It is also used after the procedure to monitor stents and grafts for signs of the blockage returning ("restenosis"). If a hematoma develops after a catheterization procedure, arterial ultrasound is also used to check the integrity of the arteries and veins in the groin.

C. Cardiology (visualizing the heart or valves): Transthoracic Echocardiography (ECHO) is a type of echocardiogram test. This type of test involves placing the transducer on the patient's chest. The device sends ultrasound waves, through the chest wall to the heart. The test gives information about the size and shape of the heart and how well the heart's chambers and valves are working. ECHO also can be done to detect heart problems in infants and children. The test also can identify areas of heart muscle that aren't contracting normally due to poor blood flow or injury from a previous heart attack. In addition, a type of ECHO called Doppler ultrasound shows how well blood flows through the chambers and valves of the heart. It can be used to detect any narrowing of the heart valves or leaking valves. ECHO can detect possible blood clots inside the heart, fluid buildup in the pericardium (the sac around the heart), and problems with the aorta. The aorta is the main artery that carries oxygen-rich blood from the heart to the organs of the body.

D. Breast: The ultrasound test is done to diagnose abnormalities present in the breasts. In addition, there are a few conditions that can benefit from such test: For example, to detect the underlying cause of breast pain, redness, swelling, etc.; to find out presence or absence of fluid inside a breast lump, to differentiate between a solid and fluid filled cyst; to perform the test on women carrying high risk of breast cancer and are not suitable for MRI; during pregnancy when exposure to x-ray is not advised; to measure the spread of a cancer; and the ultrasound images can be used as a guide for breast biopsy or breast surgery. In the case of breast imaging, if an abnormality is felt by physical exam or by the patient itself, ultrasound is the best way to find out if the abnormality is solid (such as a benign fibroadenoma or cancer) or fluid-filled (such as a benign cyst). Another example is to evaluate a palpable breast lump (a breast lump that can be felt through the skin).

An exemplary embodiment of a base according to the invention is shown in FIG. 1, and is generally indicated by arrow 100. The base is, in this embodiment, provided with a cavity 101, which is suitable to house a smart device of given dimensions. This cavity, however, can, in other embodiments, be replaced by any other connection and positioning elements, suitable to keep the smart device and the base conveniently, reversibly, physically connected to allow said base and said smart device to be moved as a single unit. In the exemplary embodiment of FIG. 1, a socket 102 is provided in the lower part of the base, in which a connector (not shown) is located. The connector is configured to electrically connect electronics of an ultrasound array located on the base to a data input port of the smart device that is to be used in conjunction with base 100. The connector can be, for instance, a USB connector such as used by an iPhone, Samsung Galaxy, Sony Experia, etc., or a different type of connector as used by other phones such Huawi, Nokia, etc.

Figure 2:
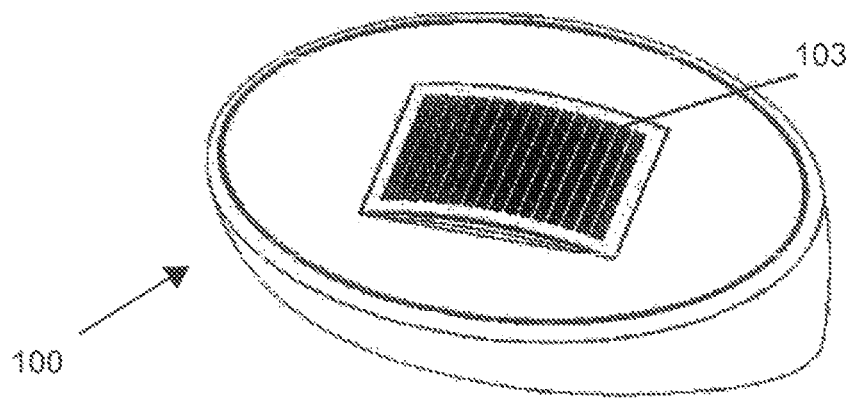
FIG. 2 is a view of the bottom of the base of FIG. 1.
Figure 3:
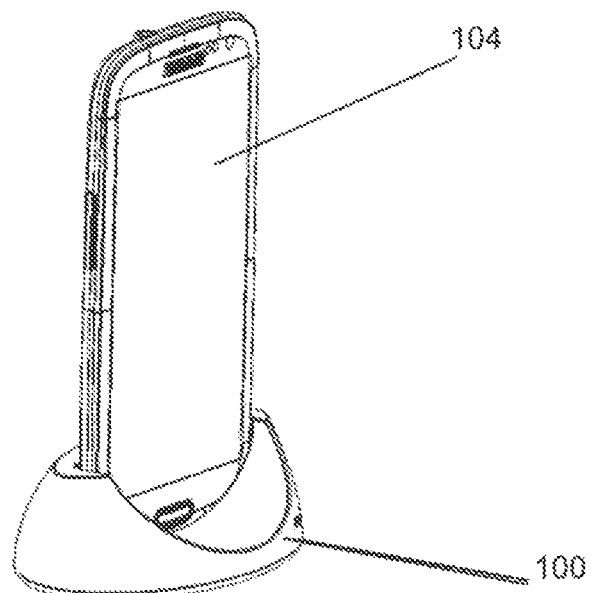
FIG. 3 is a view of the base of FIG. 1 with a smart device connected to it.

Turning now to FIG. 2, the bottom portion of the device 100 of FIG. 1 is seen. On the bottom outer surface of device 100 is located an ultrasound transducer 103. Embodiments of the ultrasound transducer 103 as well as the electronics that operates the ultrasound system, which are located between ultrasound transducer 103 and the connector in socket 102, as will be described herein below. FIG. 3 shows a smart device 100, in this example a smartphone, fitted into the cavity in base 100. The connector in the socket at the bottom of the cavity provides the electrical connection between the electronics in base 100 and smartphone 104. Additionally, the connector and the sides of the cavity connect the smart device mechanically to the base so that they can be moved together across a surface, e.g. a human's abdomen, as a single unit.

Figure 13A:
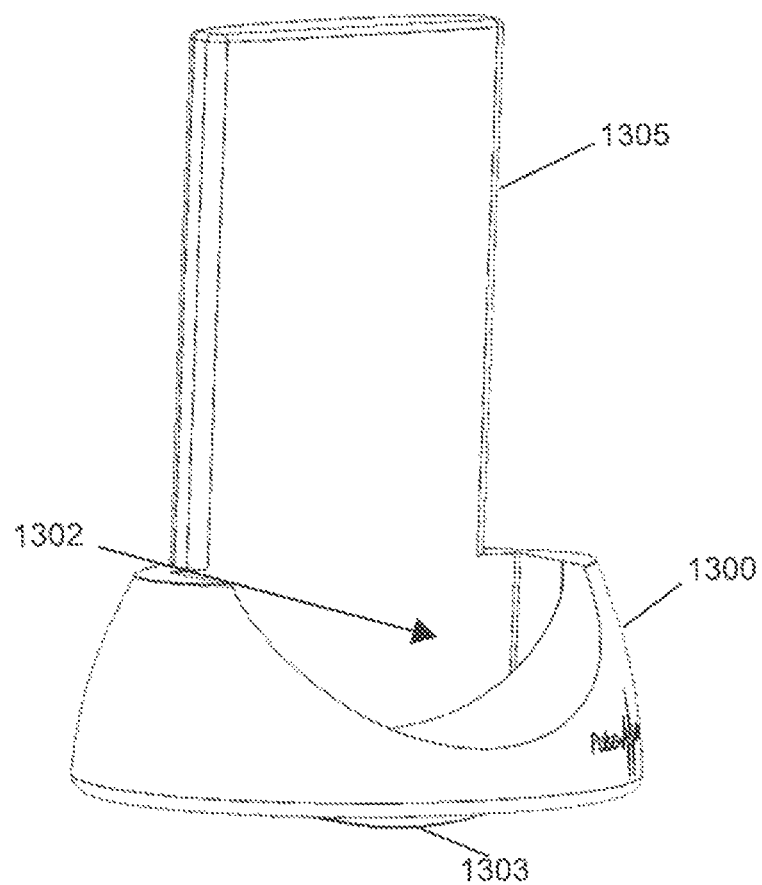
FIGS. 13A, 13B, and 13C schematically show another embodiment of the base of the invention.
Figure 13B:
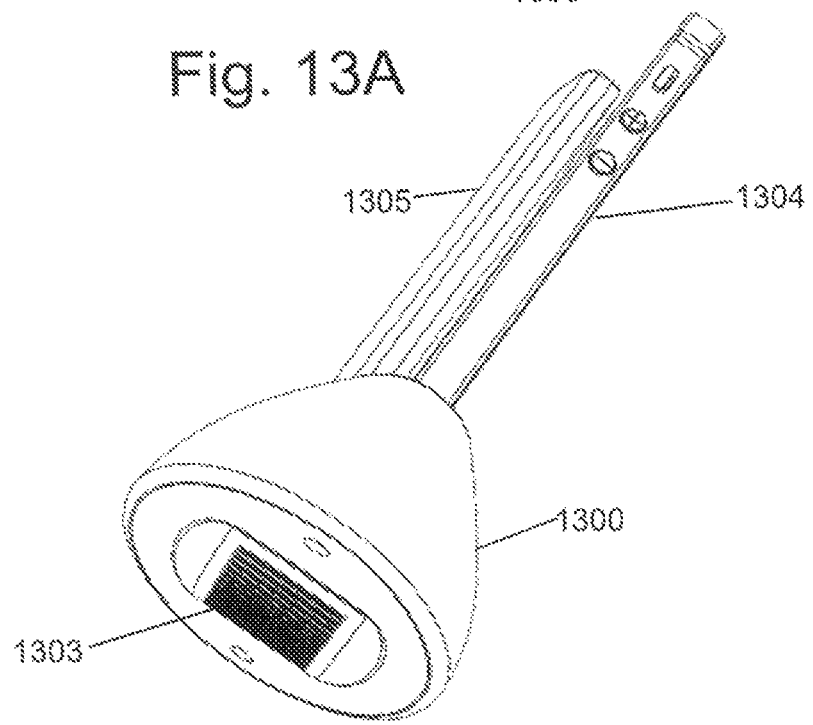
Figure 13C:
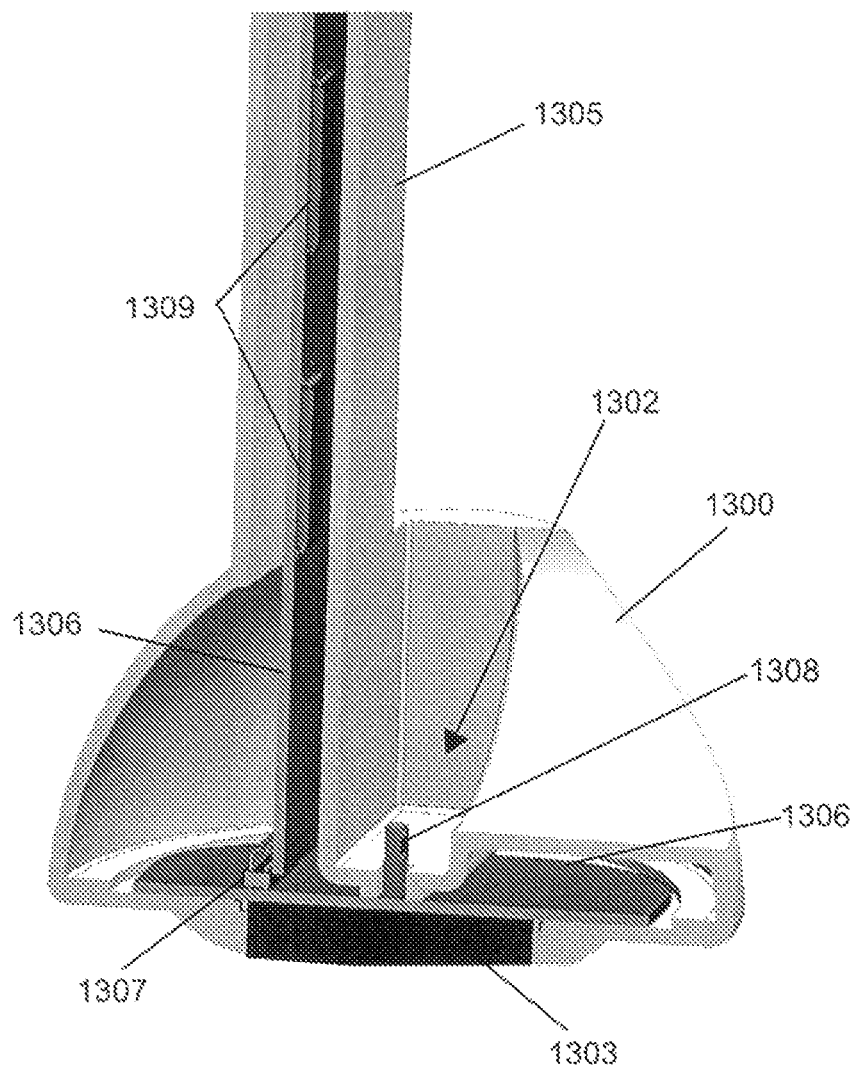

Another embodiment of the base of the invention is shown schematically in FIGS. 13A, 13B, and 13C. Referring to FIG. 13A, base 1300 comprises a lower section that is essentially like base 100 shown in FIGS. 1, 2, and 3. In this embodiment base 1300 has a planar vertical back wall 1305, which is integral with the lower section. As in the case of the embodiment described herein above, base 1300 comprises a cavity 1302 into which a smart device 1304 (see FIG. 13B) can be inserted. At the bottom of the base is ultrasound array 1303.

FIG. 13C is a cross-sectional view showing a "T" shaped PCB 1306 that is fitted into the interior of the base. Connector 1307 provides a direct connection between the ultrasound array 1303 and electronic elements 1309 mounted on PCB 1306. Connector 1308 provides, inter alia, mechanical connection between a smart device (not shown) inserted into cavity 1302 and direct electrical connection between ultrasound array 1303 and the smart phone.

The invention will now be illustrated with reference to fetal activity and the first embodiment of the base. When it is desired to check the movement of a fetus, a smart device 104 (in this example, an iPhone) is inserted into the cavity 101 and coupled to the base 100 by means of the connector in socket 102 as is illustrated in FIG. 3. Smart device 104 runs the software that performs the operations that will be described hereinafter and is used to display images created from data gathered by the ultrasound transducer.

Of course, as appreciated by the skilled person, the ultrasound transducer 103 described above could be replaced in all cases by suitable elements that are excited and generate pressure waves, such as single elements, an array of elements, a linear array, a focused array, a multi-dimensional array, i.e., a 1.5D, 2D and 3D array. The elements may be straight or curved with different shapes and can be constructed on a plane, a convex, or a concave surface. The transducer elements can be made from different materials such as, for example, Piezo, Piezo composite, and metals using know techniques, for example Silicon based substrates, CMUT (Capacitive micromachined ultrasonic transducers), PMUT (Piezoelectric Micromachined Ultrasonic Transducers), MEMS (Microelectromechanical systems), and NEMS (Nanoelectromechanical systems).

When it is desired to monitor the activity of the fetus, the smart phone 301 is turned on and an ultrasound software application is launched from the base or from the smart device or, in some embodiments part or the software resides on the base and part on the smart device.

The base 300 is now moved along the pregnant woman's abdomen and images or video generated by the ultrasound system are stored in the smart device for viewing and/or transmitting to a physician or hospital, as the case may be. In embodiments of the invention communication to and from the system can be via a unique IP address assigned to the base 300 or by using the mobile number of the smart device. Therefore the physician can contact the base via any IP communication, using a communication channel (secured or unsecured) in order to send voice instructions to be heard by the patient for example, to instruct the patient to move the base in a certain direction in order to acquire images at different positions, or the physician can send still images or video movies from the socket to a device controlled by him, such as, for instance, a PC or a mobile device with camera. Of course, like in any other ultrasound procedure, a gel, water, or other material suitable to improve matching is preferably to be used between the transducer and the skin in order to reduce noise and to provide good ultrasound propagation between the different body layers.

In another exemplary embodiment, the base includes a rechargeable battery and a DC to DC converter to convert battery voltage from (for instance) 3.7V to 9V or 20V or up to 200V to support excitation of the ultrasound transducer. Another option for supplying power to the transducer is to use a switching power supply consisting of a power stage and a control circuit. The power stage performs the basic power conversion from the battery's input voltage to the output voltage required to activate the ultrasound transducer and includes switches and an output filter. The battery can be disposable or rechargeable. Embodiments of the invention use the battery of the smart device. Conversion of voltage or current (as the case may be) is well known in the art. For example Texas Instruments TL497ACN components can convert the input voltage from a smart device to the excitation voltage required by the ultrasound transducer. The three basic switching power supply configurations in common use are the buck, boost, and buck-boost, but they are beyond the scope of this discussion.

In one embodiment, the smart device provides all the processing capability while the base provides the power for the ultrasound elements. The communication between the base and the smart device is done by a well-known protocol, for example, Bluetooth. In another embodiment, the base contains a super-capacitor (or ultra-capacitor) that stores energy, this energy is provided through a DC-DC converter to excite the elements that produce the ultrasound waves. Such elements may include piezoelectric materials as PZT, or films, PVDF, PMN-PT, PMN-XX, PIN-PMT-XX where the XX is for several derivatives of the materials, Silicon, Metal, CMUT, MEMS, NEMS, etc.

The production of the elements that produce the ultrasound waves can be purely mechanical, like crystals that are diced or sawed, and then assembled into arrays or by use of wafer technology, such as Capacitive Micromachined Ultrasonic Transducers (CMUT), Piezoelectric Micromachined Ultrasonic Transducers (PMUT) and similar configurations that use semiconductor technologies to produce the elements of the entire array. In addition, with configurations that are wafer based production, it is possible to add other components to improve the quality of signal, for example, an amplifier that is implemented on the silicon wafer and connected to the elements to amplify low signal or to implement an Analog to Digital converter, to provide digital signal for processing instead of analog, or to implement mixed analog digital circuits or components.

Once a scan is completed across the woman's womb, the smart device can be separated from the base and, using software provided in or to the smart device, the recorded ultrasound image or a series of images that form a video movie of the fetus' activity, can be viewed on its screen. If the smart device is provided with communication capabilities, and if deemed necessary, the recorded images can be forwarded to a physician or other healthcare specialist for viewing, unless transfer has already been affected in real time, as in some embodiments of the invention in which communication capabilities exist in the base. In this respect it should be understood that it is only necessary, according to the invention, that the base and the smart device connected to it, cumulatively have communication capabilities. Thus, for instance, the smart device may be an MP4 recorder that does not have communication capabilities, but those may be embodied in the base. Conversely, in another embodiment of the invention the base may not have any communication capabilities, but the smart device may be a smart phone with communication capabilities. In both of these cases, the smart device and the base communicate with each other via the connector in the socket in the base. Of course, it is possible to have communication capabilities in both the base and the smart device, and to use the one that is best suited for the specific operation involved. The video format used in conjunction with the invention can be any suitable format, such as, for example, a standard video format, e.g., quicktime, WMV, AVI, FLV, MP4, and DICOM.

Figure 4A:
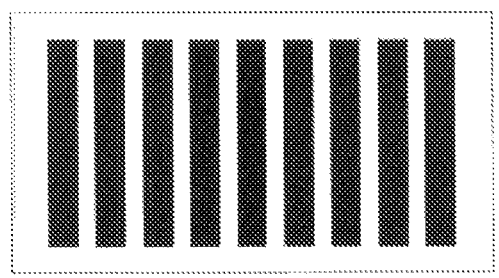
FIG. 4A to FIG. 4F that schematically illustrate a variety of ultrasound elements suitable for use according to the invention.
Figure 4B:
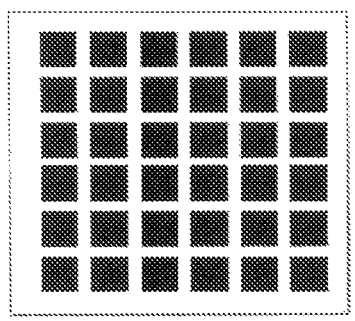
Figure 4C:
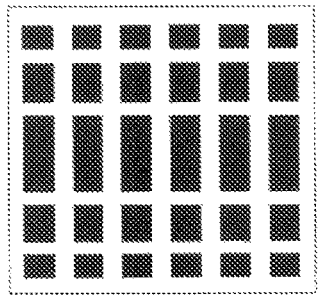
Figure 4D:
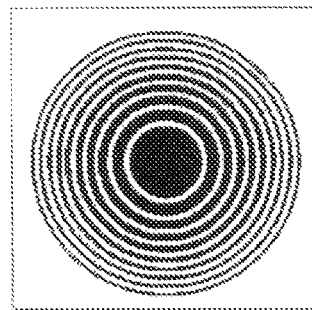
Figure 4E:
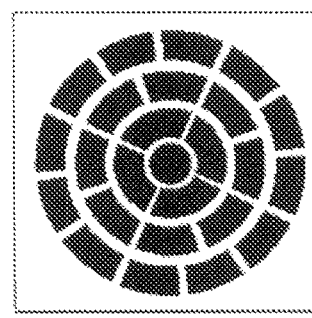
Figure 4F:
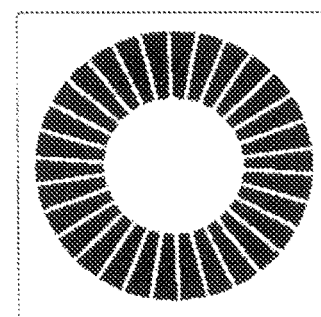

The ultrasonic transducer can have a variety of configurations, some of which are schematically illustrated in FIG. 4A through FIG. 4F. FIG. 4A shows a 1D linear array that produces a straight beam that focuses in one axis at different depths and angles and divergence that increases with angle and depth. FIG. 4B shows a 2D square array that has steering capability in three dimensions with spherical or single-axis focus. FIG. 4C shows a 1.5D square or rectangular matrix array that has steering capability and focuses on one axis at different depths and angles, thereby reducing artifacts. FIG. 4D shows a 1D annular array that has spherical focusing at different depths. This array is very good for detecting small reflectors but does not have steering. FIG. 4E shows a 2D segmented annular array that produces an elliptical or spherical beam with steering capability at different depths and angles. FIG. 4F shows a 1D circular array that produces an elliptical or spherical beam with steering capabilities. Each array will require different connections to the smart device and different excitation signal. This however is achieved by the software and the processing components.

According to one embodiment of the invention, the ultrasonic transducer for a single element or array is provided in close positioned relationship with the electronics that operate it. In other embodiments of the invention, the electronics, or at least a part of the electronics, is an integral part of the smart device. In one embodiment of the invention the ultrasonic array is manufactured integrally on a semiconductor chip that also contains the main electronic parts of the system needed to operate it. In another embodiment of the invention the ultrasonic array is separate from the semiconductor layer, but it is connected to it via a suitable connector.

Herein the term "ultrasonic" should be understood in its broad meaning. The array can be constructed from one or more elements, the ranges of frequencies are different according to the specific application and can range from 1 MHz to 20 Mhz, central frequency, depending on the situation and the type of medical examination, but can easily be provided in a 1 to 35 Mhz range for other applications. Typical bandwidths can vary from 500 KHz to 27 MHz, depending on the application. It is also possible to construct a piezo or piezo composite element that is rotated by means of an electrical motor to generate a continuous video with no array at all. Manufacturing such layered systems is known in the art, for instance as discussed in U.S. Patent Application Ser. No. 2009/0082673, filed Mar. 26, 2009 by Lu et al., for "Detecting nuclear, electromagnetic, or ultrasonic radiation ultrasonic structure of transducer or probe assembly", and as discussed by Dausch et al. (http://www.rti.org/pubs/cardio-vascrevascmed-v14p157_ddausch.pdf).

Basic Ultrasound Principles

Ultrasound machines form images of biological tissue by transmitting focused beams of sound waves into the body and using the differences in strength and delay of the reflected sound waves to reconstruct the image of the structure. This is usually accomplished with a piezoelectric- (or other materials) based transducer array situated at the end of a probe module, which is pressed against the body being imaged. The piezoelectric transducer elements are stimulated by high-voltage pulses (+/−5 VPP to +/−300 VPP), causing the elements to vibrate, which in turn generates the transmitted acoustic waves. The elements in the array are usually phase aligned with each other to create a focused beam of acoustic waves at a predetermined location and distance in the body. As these incident waves pass through the structure, differences in the acoustic impedance between layers of tissue cause reflections back to the transducer.

Immediately after transmitting acoustic waves, the transducer elements change their role to become detectors, picking up the reflected signals. A representative image of the body is formed by focusing the transmit beam along many scan lines in the area being analyzed and then reassembling them in the backend electronics of the ultrasound machine to form a 2-D image.

While the transmit electronics, or transmit beamformer, have the challenging task of transmitting waves across the image range with the correct phase alignment, the receive electronics have the complex and highly proprietary responsibility to assemble the received acoustic reflections into images. The receive electronics, or receive beamformer, must properly phase align the individual receive channels to set the correct focus depth, filter the incoming data, demodulate the waveform, and then sum all channels together to form a scan line. This process is repeated for each scan line; then all the scan lines are assembled, interpolated, and filtered to form the final image.

Architecture

At a very high level, ultrasound systems consist of three distinct processing blocks: the analog frontend (AFE), the beamformer with frontend processing, and the backend.

Analog Frontend (AFE):

The AFE is a highly specialized system for ultrasound applications that can be implemented in the form of a fully integrated single-chip per each 2, 4, 8, 16, 32, etc. channels or in a multichip per channel custom solution. To handle the large dynamic range of the transducer receive signals, a variable gain amplifier (VGA) or time gain compensator (TGC) is used to map the signal to the smaller dynamic range of the analog to digital converter (ADC).

Beamformer:

The ultrasound beamformer consists of two parts. The transmit beamformer (or Tx beamformer) that is responsible for initiating scan lines and generating the timed pulse string to the transducer elements to set the desired focal point in the structure. The receive beamformer (or Rx beamformer) that is responsible for receiving the echo waveform data from the analog frontend, and collating the data into representative scan lines through filtering, windowing, summing, and demodulation. The two beamformer blocks are time synchronized and continuously pass timing, position, and control data to each other.

The Tx beamformer is responsible for steering and generating a timed, digital pulse string that gets externally converted into high-voltage pulses for the transducer. The delay is calculated in real-time, based on the required instantaneous location of the focused ultrasound beam for the given scan line. This is a fairly small block, requiring a very small logic resource of the Tx beamformer. It includes a timing generator and pulse shaping, and typically has a parallel interface to external DACs.

Figure 5:
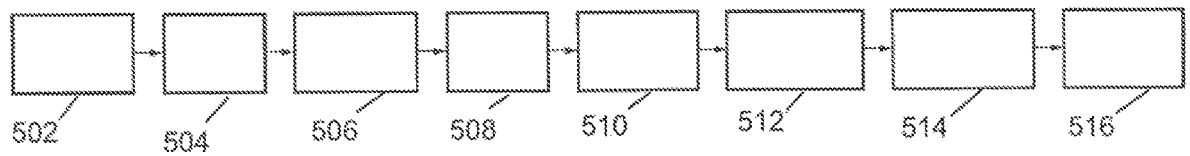
FIG. 5 is a block diagram showing the processing steps and sub-blocks of an embodiment the receiver beamformer.

The Rx beamformer parses the raw transducer Rx data to extract and assemble ultrasound scan lines. It is a usually implemented by FPGA (Field Programmable Gate Array) or DSP (Digital Signal Processing). A summary of an exemplary processing steps and sub-blocks of the Rx beamformer is shown in FIG. 5. Each step up to summation 516 is performed per channel; the remaining steps are performed per scan line. This is a typical processing flow. Rx beamforming can be performed in the frequency domain, time domain, or by other proprietary methods.

The steps shown in FIG. 5 are:
Data Capture 502: Deserializes the incoming LVDS data, synchronizes the clocks, and buffers the data for processing.
Sample 504: Oversamples the incoming data to enable better accuracy in the subsequent delay process.
Interpolation filter 506: Assists to improve image accuracy by further upscaling and adjusting for delay inaccuracies.
Delay/Focus 508: Data is delayed on each channel to adjust for the position of the focal point relative to each transducer receive element. The timing here is synchronized with the Tx beamformer and can be altered by the system user in real time to steer the beam and focal point.
Windowing/Apodization 510: Removes spatial image echoes (side lobes) that naturally occur in a beam response.
Logarithmic Compression 512: Reduces the dynamic range of the data to acceptable levels for image processing and display.
Demodulation 514: Demodulation extracts the final scan line from the echo carrier frequency range. This process often includes envelope detection, down conversion, decimation, filters, and matched filters. Hilbert transform is typically used for envelope detection.
Summation 516: Sums all the channels together to create final scan line representation.
Backend Processing:
The backend processing block typically includes B-mode, M-mode, Doppler, and color flow processing functions. These functions operate simultaneously and perform a variety of actions. The B-mode processing engine receives the demodulated and compressed scan lines, and uses interpolation and gray scale mapping to form 2-D gray scale images from the scan lines. The M-mode compares data points over time to identify motion, velocity, and the location of the motion in the source.

Doppler processes data from the Doppler-specific analog frontend and produces accurate direction and velocity information. The color flow processing block maps color scale to the motion data to indicate velocity and direction and overlays it on the gray scale image from the B-mode function. The backend then cleans and adjusts the images to suit the requirements of the sonographer and the display being used, and stores, displays, and transmits static and video outputs. A number of different enhancement techniques can be deployed in ultrasound systems to reduce speckle, improve focus, and set contrast and gray scale depth. A few examples include:
Angle Compounding—Used for speckle reduction by comparing views from different angles of the same focal point and combining them for a weighted sum. Requires multiplying the data by a 2D matrix to correlate coordinates from each angle.
Wavelet Decomposition—Used for speckle reduction. Wavelet decomposition evaluates different frequency regions of the signals and determines if down-conversion is needed.
Anisotropic, Bilateral Filtering—For speckle reduction.
Histogram Equalization—Creates a balanced contrast and quality for images.
Frame Smoothing—Utilizes a low pass filter for processing to smooth images by averaging and adjusting adjacent pixels.
Edge Detection—Uses sharpening filters such as high-pass, high-boost, and derivative to remove blur in the image.

Figure 6:
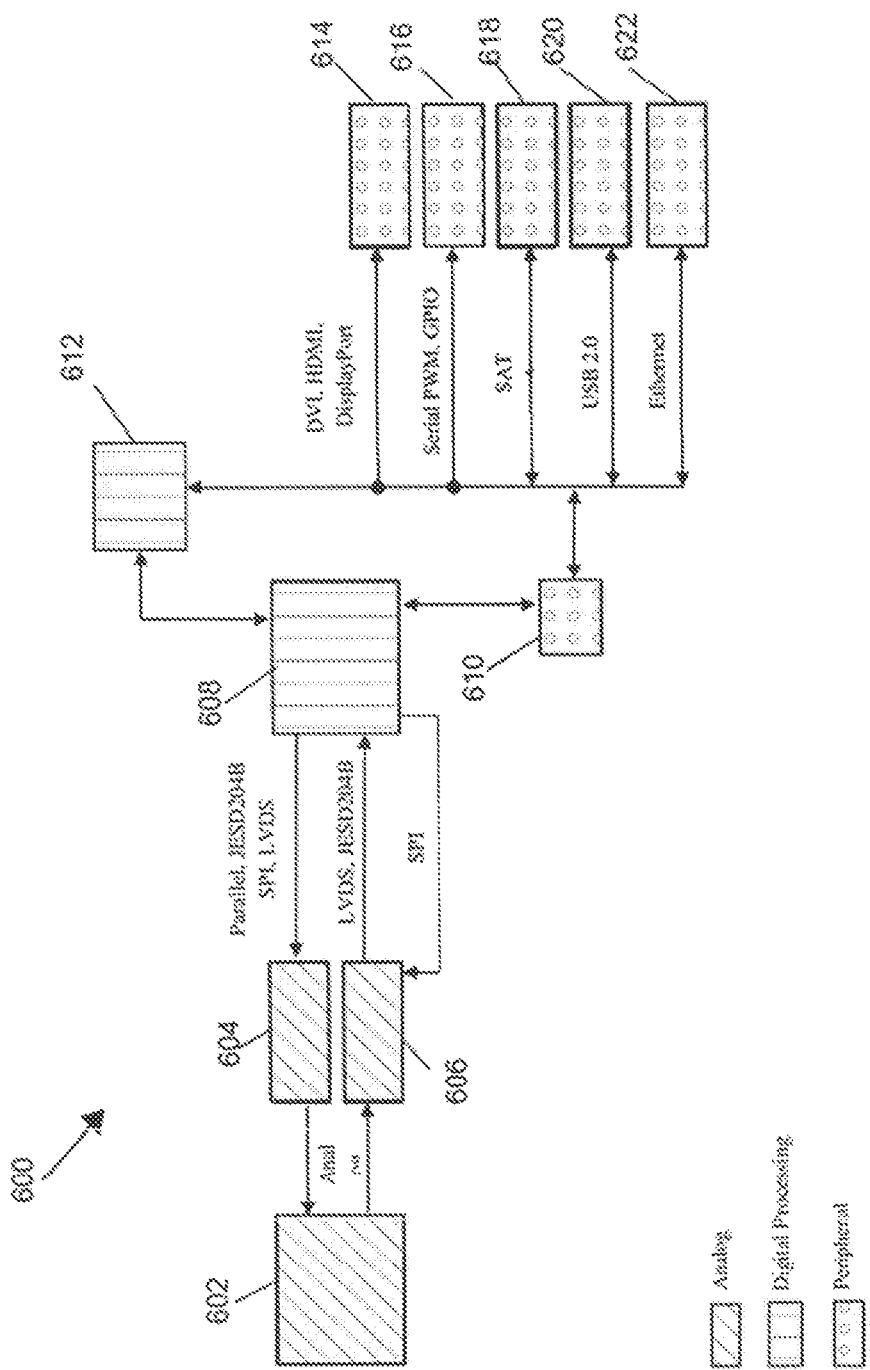
FIG. 6 is a block diagram that schematically shows the architecture of an embodiment of an ultrasound system that can be used in the invention.

FIG. 6 is a block diagram that schematically shows the architecture of an embodiment of an ultrasound system that can be used in the invention. The ultrasound system 600 comprises: transducer 602, AFE Tx 604, AFE Rx 606, Beamformer Frontend 608, SDRAM 610, Backend 612, and the Peripherals—Display 614, Audio 616, HDD 618, User Input 620, and Network 622. Transducer 602, AFE Tx 604, and AFE Rx 606 employ analog processing. Beamformer Frontend 608, SDRAM 610, and Backend 612 employ digital processing. The arrows in FIG. 6 represent the communication channels and examples of protocols that can be used to communicate between the blocks. They are: 604-602 analog signals; 602-606 analog signals; 608-604 parallel, JESD204B, SPI, LVDS; 606-608 LVDS, JESD204B; 608-606 SPI; 612-608 SRIO, PCIe, LVDS; 610-612 and peripherals DDR2, DDR3; 612-514 DVI, HDMI, Display Port; 612-616 Serial PWM, GPIO; 612-618 SATA; 612-620 USB 2.0; and 612-622 Ethernet.

Figure 7:
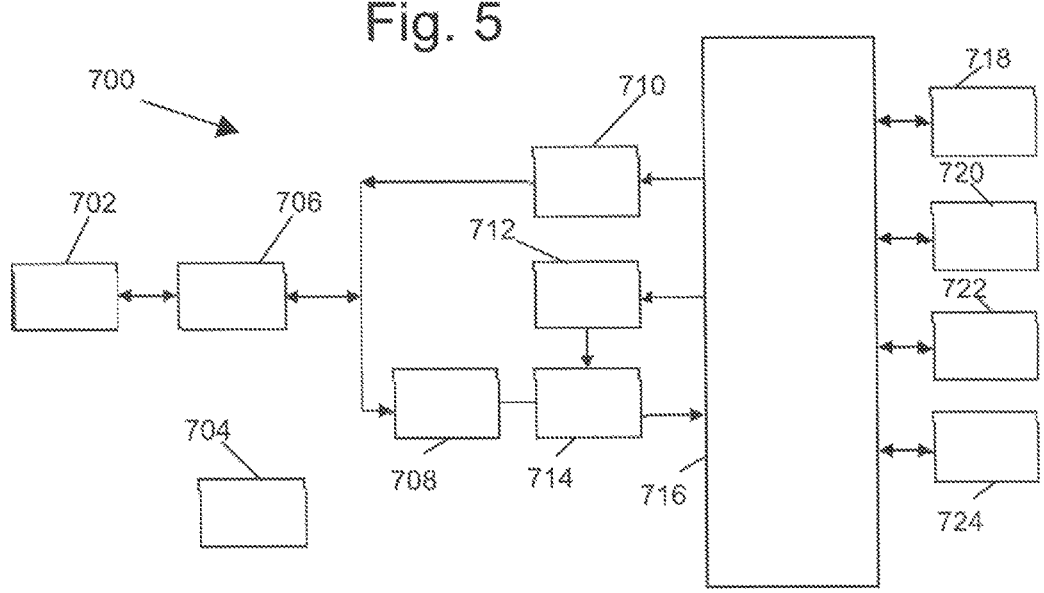
FIG. 7 is a block diagram that schematically shows the architecture of another embodiment of an ultrasound system that can be used in the invention.

FIG. 7 is a block diagram that schematically shows the architecture of another embodiment of an ultrasound system that can be used in the invention. In this embodiment ultrasound system 700 comprises: probe 702, power supply 704, HVSW (high-voltage switch) 706, T/R (Transmitter/Receiver) 708, TX (Transmitter) 710, ATGC (Automatic Time Gain Compensation) 712, AFE (Analog Front End) 714, CPU (Central Processing Unit), 716, DDR (Memory) 718, FLASH (Memory) 720, USB-OTG (Universal Serial Bus Once To Program) 722, and LCD (any display such as liquid crystal polymer or similar) 724.

Figure 8:
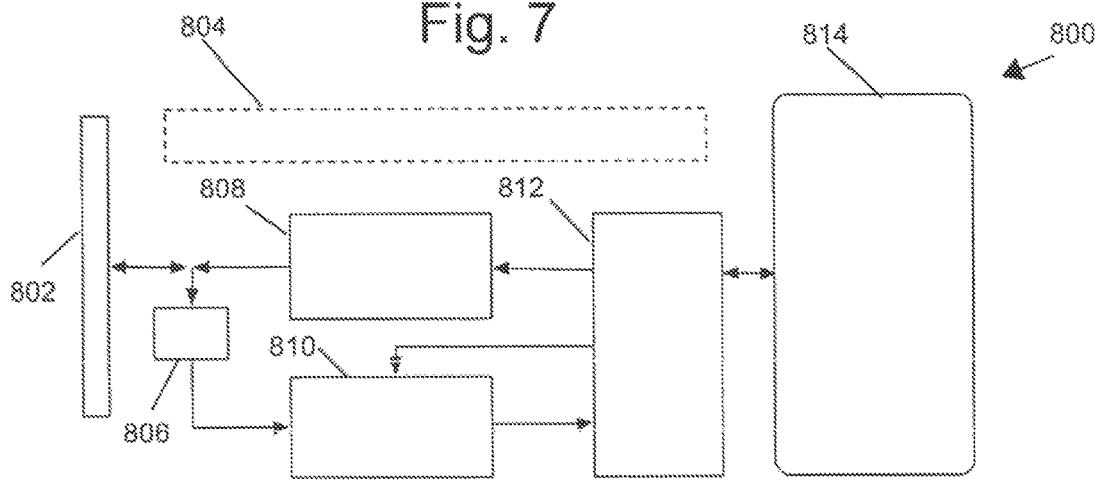
FIG. 8 is a block diagram that schematically shows the architecture of an embodiment of an ultrasound system that can be used in the invention.

FIG. 8 is a block diagram that schematically shows the architecture of another embodiment of an ultrasound system that can be used in the invention. In this embodiment, ultrasound system 800 comprises: probe 802, battery power supply 804, T/R (Transmitter/Receiver) switch 806, pulser (high-voltage and high-speed pulse generator) 808, AFE (Analog Front End) 810, FPGA (Field-Programmable Gate Array) 812, and smart device 814.

Figure 9A:
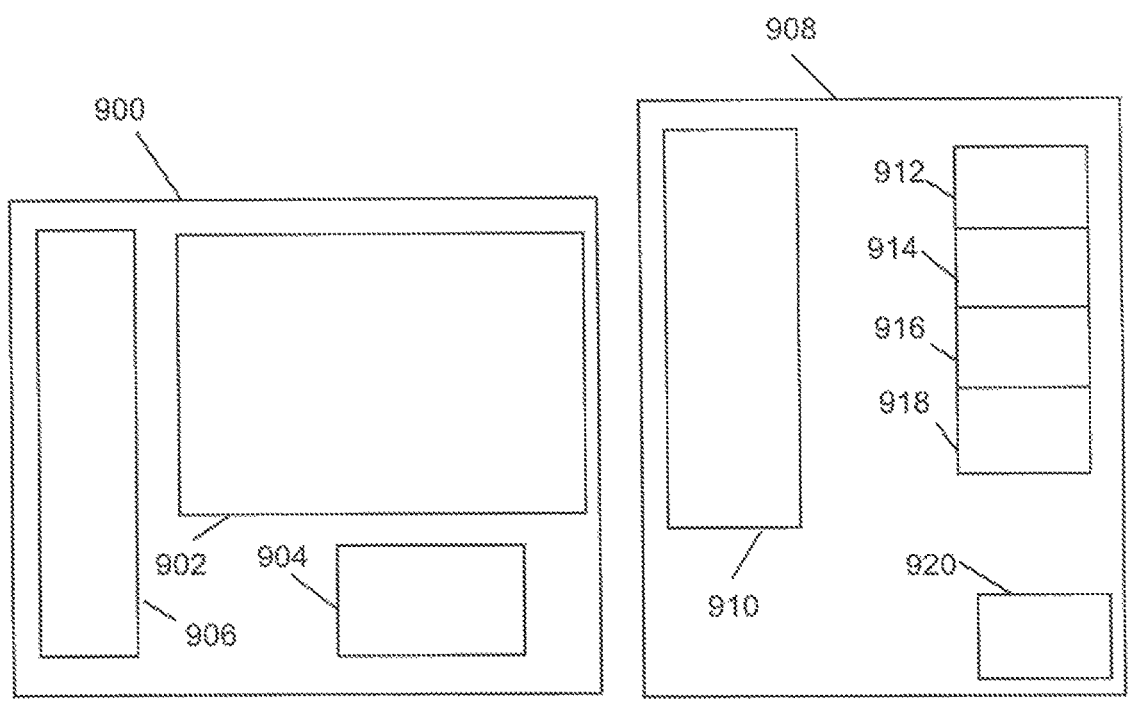
FIG. 9A schematically shows an embodiment of the system of the invention that employs a fully integrated AFE in the base.

FIG. 9A schematically shows an embodiment of the system of the invention that employs an AFE fully integrated in the base. In this embodiment base 900 comprises an electronic circuit 902, a DC to DC converter 904 and an ultrasound transducer 906. Electric circuit 902 comprises one FPGA with an integrated microcontroller component or a CPU, both of which implement all blocks of the ultrasound system, i.e. all analog and digital components including Analog Front End (Receiver, Transmitter, and switches). These components are implemented as one Mix ASIC or two chips. According to one embodiment of the invention, the transducer itself is constructed on one layer of a PCB and connected through vias to the FPGA component circuitry that is mounted on a second layer of the FPGA or CPU. The smart device 908 comprises a CPU 900, memory 912, USB connection 914, display 916, peripherals 918, and a power supply 920. In this fully integrated AFE the VGA/TGC in base 900 is controlled by logic in smart device 908 through a bus, for example a Serial Peripheral Interface (SPI) interface, but can also be implemented through other protocols.

In another embodiment, all of the blocks are implemented in several existing chips that are available in the mobile device. The AFE is implemented by using the existing AFE of the mobile device on a time base. The mobile processor includes several cores, and this embodiment implements most of the software on the assigned cores that were designated by the device manufacture for external applications. One such embodiment uses the battery and voltage to excite the transducer from the existing battery of the mobile device, and uses the mobile device display to display the images or video. Thus, in this embodiment of the invention, except for the elements that generate the ultrasound, all other processing blocks, circuits or chips exist in the mobile device and can therefore be exploited to create an inexpensive device of the invention that can function with them.

Figure 9B:
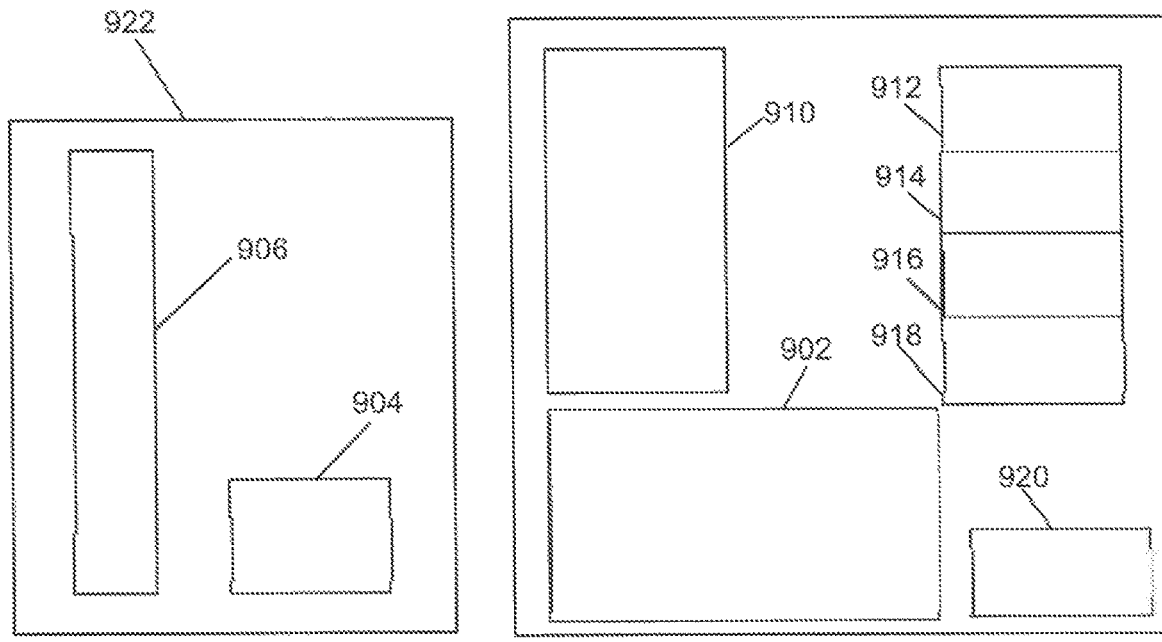
FIG. 9B schematically shows an embodiment of the system of the invention without a fully integrated AFE in the base.

FIG. 9B schematically shows an embodiment of a solution without a fully integrated AFE in the base. In this system the electronic circuit 902 is removed from base 922 and is located in smart device 924. In this case a digital to analog converter (DAC) is typically driven by logic to control the variable gain that produces an analog waveform that controls the VGA/TGC. The ADC data is serialized and transferred to the digital processing devices via LVDS (Low Voltage Differential Signal) or similar technique or device.

Another embodiment of the apparatus may use a more advanced chipset that is included in the smart device. In this case the base includes the transducer or array of elements for transmitting the ultrasound and also acts to receive the reflected pressure waves from the internal organ. The chip set can be discrete (one-two chips or more) or implemented by an ASIC in the existing chips of the mobile phone. For example, using existing A/D, one or two cores that exist in the processor and analog front end chip, etc. If the DC to DC cannot be implemented in the same ASIC, then it will be an additional component. In this way the cost of the system is reduced to the cost of the base. The implementation of the chipset is straightforward. It is possible to implement the Beamformer such that different types of focusing can be supported: (a) fixed focus, (b) several focal zones, (c) dynamic focusing, and (d) pixel-based focusing. The Analog Front End (AFE) is also implemented in an ASIC or it is possible to implement each function of the AFE with existing hardware architecture or to combine it with software that manages the process and the different functions.

For example, Qualcomm's SANPDRAGON MSM 8960 processor and chip set are used in many mobile smart phones. This processor can integrate the entire requirements for beamforming. Another chip which communicates with the 8960 processor can integrate the analog front end. In addition, it is possible to use a more advanced hardware architecture and to implement the entire requirement for the ultrasound in a mixed analog/digital ASIC. This is possible since the antenna of the mobile phone also uses AFE.

Moreover, in another embodiment, the application will be stored as software in the servers of the mobile network operator or in the cloud. A Business-To-Business (BTB) customer, i.e., a pregnant woman, will activate the service by using her smart device and the application, and will only need the base comprising the ultrasound transducer to house the smart device. The data (including images of the fetus) can be displayed or stored and sent to the hospitallclinic from the operator or the cloud. All data integrity, encryption if necessary, and other data activities can be supported from the operators' servers or the cloud.

It is possible to use any suitable cloud service, for instance existing cloud services which enable external users to connect to the cloud and store files, such as Amazon S3 API. In addition, a virtual server can be implemented in the Amazon (or similar) cloud that enables further processing of data such as data mining. It is also possible to use the cloud service to deal with secured monetary transactions and to store all required data within the cloud. Another embodiment is to connect the base via any suitable communication protocol to the cloud directly, as can be done, for example, with Microsoft's Azure, Oracke, and Amazon cloud platform.

Another aspect of the invention relates to the secured communication between a physician and a patient who uses the base. In one embodiment of the invention each base has an internal code (characters and numbers) that provides its unique identification. It is possible to create a secured communication, similar to a virtual private network over the WI-FI or any other communication network. In this way, the physician can take over the control of the application in the smart device and can record, send images or video from the system to his computer, to the cloud or to any other desired location. The communication can be encrypted using private or public keys from one side or from each side, or alternative security arrangements can be provided. In addition, in the case that the patient would like to send images or video to a medical center or to the physician, similar methods may apply.

As will be apparent to the skilled person, the system of the invention also allows recording images and sounds of the heartbeats of the fetus in the base or the smart device and/or displaying the images and playing out the sounds (for instance, using the speakers of the smart device or a speaker provided in the base, or a remote speaker), thus accomplishing two purposes at one time. Moreover, the invention makes it possible for the general public to monitor fetal activity without the need to acquire expensive equipment.

Figure 10B:
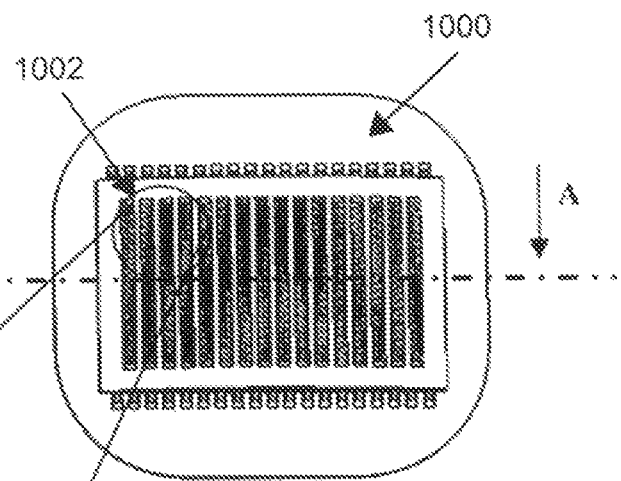
FIG. 10B is a top view of the transducer shown in FIG. 10A.
Figure 10C:
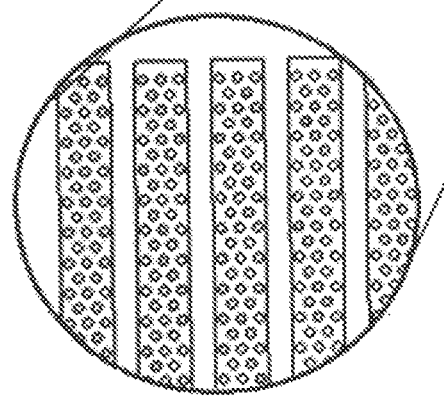
FIG. 10C is a magnified view of portion of the transducer shown in FIG. 10A that symbolically shows the individual PMUT structures that comprise the transducer elements.
Figure 10A:
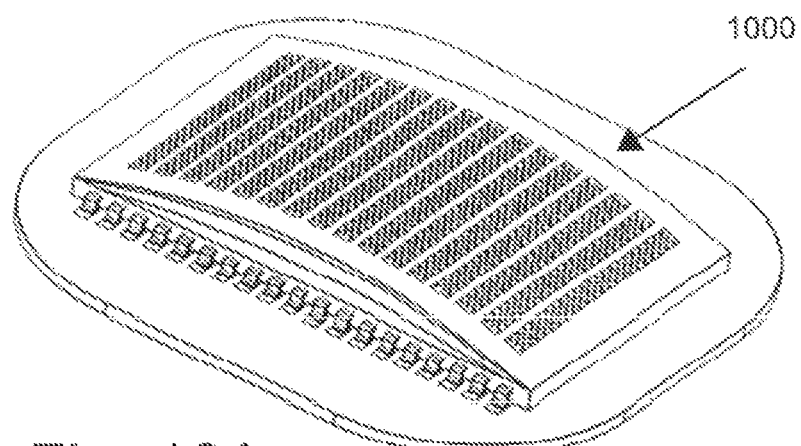
FIG. 10A is a schematic perspective view of a PMUT ultrasound transducer that is comprised of 16 elements.

FIG. 10A is a schematic perspective view of a PMUT ultrasound transducer 1000 that is comprised of 16 elements. FIG. 10B is a top view of the transducer shown in FIG. 10A and FIG. 10C is a magnified view of portion 1002 of transducer 1000 symbolically showing the individual PMUT structures that comprise the transducer elements When viewed from the side, in the direction indicated by the arrows A-A in FIG. 10B, transducer 1000 has a convex shape.

Figure 10D:
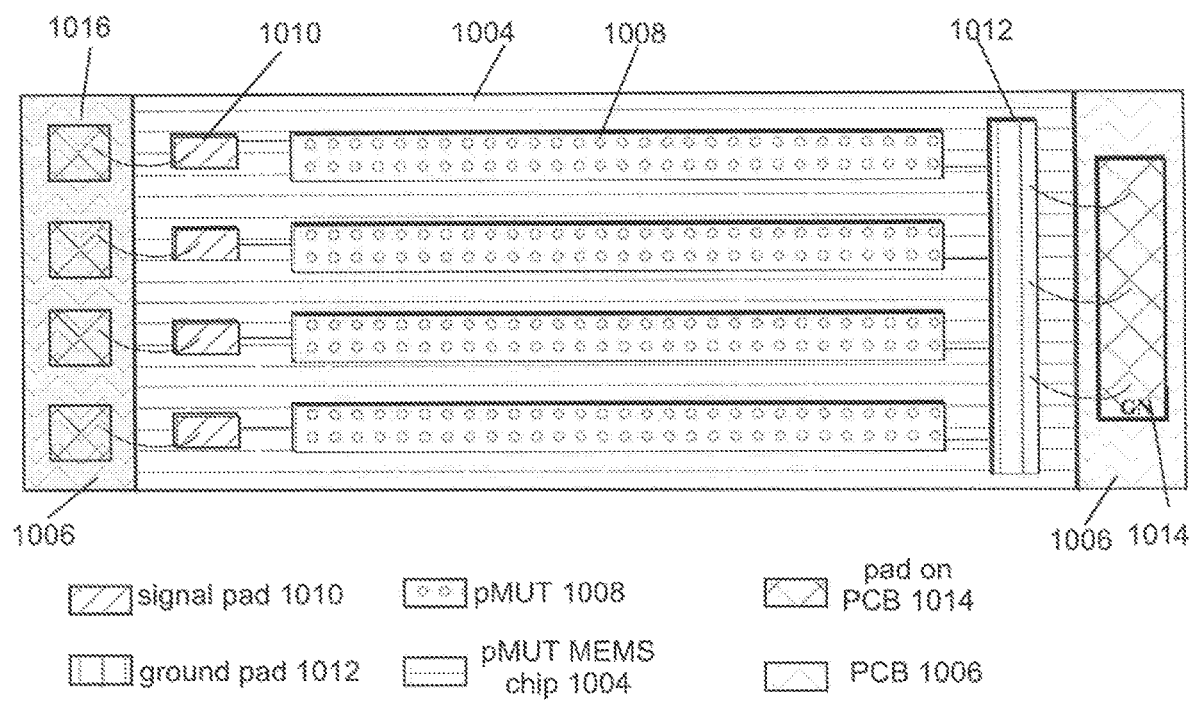
FIG. 10D shows the electrical connections to four of the elements of the transducer of FIG. 10A.

FIG. 10D shows the electrical connections to four of the elements of the transducer of FIG. 10A. Seen in the figure are PMUT elements 1008, signal pads 1010 and ground 1012 on PMUT chip 1004 and signal pads 1016 and ground 1014 on PCB 1006. Note that the structure of the elements based on PMUT, there are two options to connect the signal and ground pads, either using common ground for all elements as in FIG. 10E or it is easily possible to provide a separate ground for each element.

A prototype of a transducer has been built in order to demonstrate the feasibility of the invention. The transducer is similar to that described with respect to FIG. 10A to FIG. 10E. It is comprised of 32 similar strips filled with PMUT elements on a convex substrate. The transducer operates at a central frequency of 3.5 MHZ±10%. It has a pitch of 0.5 mm, elevation 12 mm, elevation focus 85 mm, bandwidth ~80%, and has a Samtec FTMH-120-02-F-DV-ES connector.

FIG. 11A and FIG. 11B are graphs showing respectively the time and frequency responses for one element out of the 32 elements in the prototype transducer. FIG. 11 C is a graph showing the variation in sensitivity for the elements in the 32 element prototype transducer. The following three tables summarize the features of these three graphs.

TABLE 1

Element 16 Time Response

| | |
|---|---|
| Sensitivity | $V_{pp}$ = 264 mV |
| Axial Resolution - 6 dB | AxR = 328 ns |
| - 20 dB | AxR = 813.7 ns |

TABLE 2

Element 16 Frequency Response

| | - 6 dB |
|---|---|
| Low cut off frequency | 1.8 MHz |
| High cut off frequency | 4.8 MHz |
| Center frequency = Fc | 3.3 MHz |
| Bandwidth | 3.0 MHz |
| Bandwidth/Fc | 91% |

TABLE 3

Element Sensitivity Variations

| | AVG | MIN | MAX |
|---|---|---|---|
| App | 275 mV | 264 mV | 287.1 mV |
| Axial Resolution - 6 dB | 327 ns | 319 ns | 333 ns |
| Axial Resolution - 20 dB | 828.5 ns | 790.4 ns | 1.2 μs |
| Bw/Fc - 6 dB | 91% | 89% | 93% |
| Fc | 3.3 MHz | 3.2 MHz | 3.3 MHz |

FIG. 12A is to activate the ultrasound transducer a block diagram illustrating the main blocks of a software based ultrasound system. FIG. 12B is a block diagram illustrating the main interactions between the hardware components of the system.

The software processing carried out by the system of the invention will now be described for the B-Mode. A similar presentation, however with some changes in signal processing applies for M-Mode and Doppler mode. FIG. 12 C and FIG. 12D are block diagrams illustrating respectively the main steps of the B-mode and Color-flow software processing. A color-flow image consists of a pseudo-color flow image that is overlaid on top of a 2D B-mode image. Thus, the ultrasound system needs to simultaneously acquire and process the B-mode data as well as color-flow data.

Figure 12C:
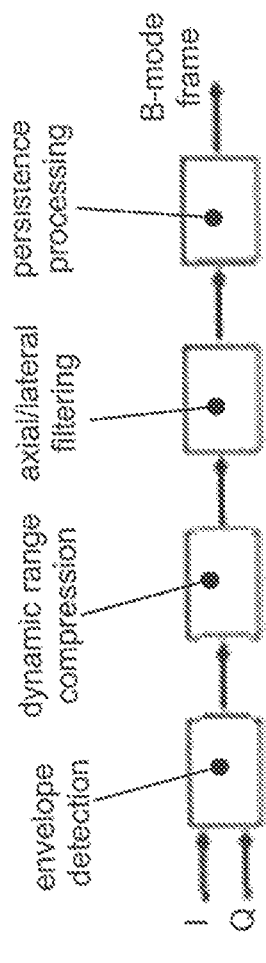
FIG. 12A is a block diagram illustrating the main blocks of a software based ultrasound system.
FIG. 12B is a block diagram illustrating the main interactions between the hardware components of the system.
FIG. 12 C and FIG. 12D are block diagrams illustrating respectively the main steps of the B-mode and Color-flow software processing.
Figure 12D:
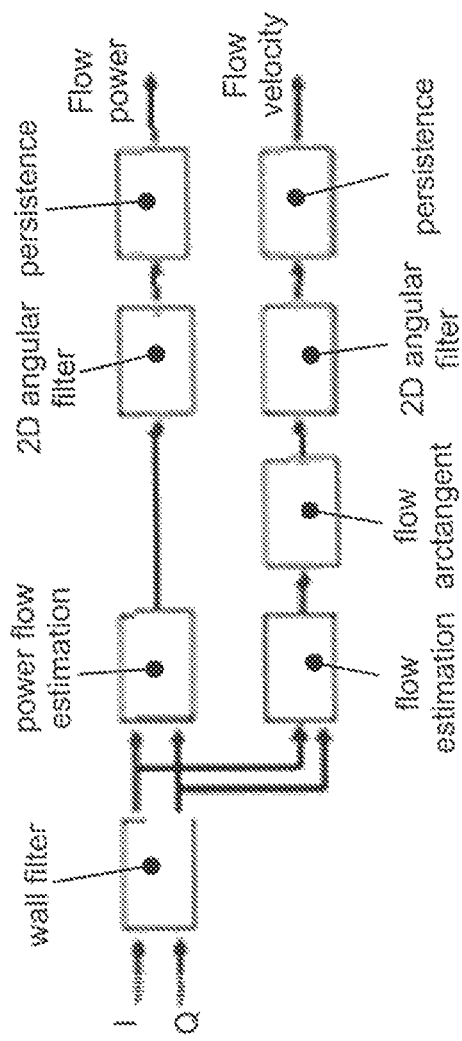

Referring to FIG. 12C, B-mode imaging computes the envelope of complex vector in the envelope detection block. The dynamic range of the envelope is therefore logarithmically compressed. Envelope detection and dynamic range compression operate on multiple vectors to create a frame of B-mode data. Spatial filtering is performed on the frame to remove noise and enhance edges. It is possible to implement the spatial filter with a 2D filter with a 8×8 or 16×16 kernel in the lateral and axial directions. Persistence processing performs temporal filtering with two consecutively acquired frames to reduce noise and speckle.

Referring to FIG. 12D, scan conversion transforms the frame to Cartesian coordinates of the raster display. The main computing blocks for color-flow processing include the wall filter, flow autocorrelation, flow arctangent, flow power estimation, 2D angular and linear filters and persistence as shown in Figure d. The received ultrasound data contain large undesired clutter (low-frequency reflections from stationary/slow moving tissues, typically vessel walls) in addition to the desired small signals generated by the moving blood cells. The wall filter is employed to remove the clutter. A high pass FIR filter is used to attenuate the clutter from the demodulated signal, I and Q. Since the characteristics of the cluster and flow signals depend on the anatomical region of the body being scanned, the number of taps and the cut off frequency of this filter need to be capable of being varied. Autocorrelation method is used to estimate the velocity. The phase of the first lag of autocorrelation of an ensemble can be used in estimating the flow velocity. Flow autocorrelation and flow arctangent estimate the flow velocity from wall-filtered data. The flow power is also estimated from the wall-filtered data. Noise is reduced by 2D filtering and persistence processing. The 2D linear filter could be, for example, 3×3 in the axial and lateral directions while the 2D angular filter could be, for example, 7×7. Persistence produces a weighted average of pixel values from two consecutively acquired velocity or power images for the corresponding output image. The scan conversion block converts the B-mode, velocity and power data from polar coordinates to Cartesian coordinates for raster display.

The examples used to describe the invention herein above relate to the use of the system of the invention by non-professionals in a home environment, but it should be obvious that the system of the invention could be very usefully employed by health care personnel either in or out of a clinic or hospital. As already stated above, the invention is meant to cover the use of any system of the type described above, at different ultrasound frequencies, number of elements, type of signal, shape of the ultrasound beam, in but not limited also to the following fields:

a. Anesthesiology: Ultrasound is commonly used by anesthesiologists (Anaesthetists) to guide injecting needles when placing local anaesthetic solutions near nerves.

b. Angiology: Duplex ultrasound (B Mode vessel imaging combined with Doppler flow measurement) is used daily in angiology to diagnose arterial and venous disease all over the body.

c. Cardiology: Echocardiography is an essential tool in cardiology for to diagnosis e.g. dilatation of parts of the heart and function of heart ventricles and valves d. Emergency Medicine: Point of care ultrasound has many applications in the Emergency Department, including the Focused Assessment with Sonography for Trauma (FAST) exam for assessing significant hemo-peritoneum or pericardial tamponade after trauma. Ultrasound is routinely used in the Emergency Department to expedite the care of patients with right upper quadrant abdominal pain who may have gallstones or cholecystitis.

e. Gastroenterology/Colorectal surgery: In abdominal sonography, the solid organs of the abdomen such as the pancreas, aorta, inferior vena cava, liver, gall bladder, bile ducts, kidneys, and spleen are imaged. Sound waves are blocked by gas in the bowel and attenuated to different degrees by fat, therefore there are limited diagnostic capabilities in this area. The appendix can sometimes be seen when inflamed (as in e.g.: appendicitis). Endoanal ultrasound is used particularly in the investigation of anorectal symptoms such as fecal incontinence or obstructed defecation. Ultrasound images the immediate perianal anatomy and is able to detect occult defects such as tearing of the anal sphincter.
f. Head and Neck Surgery/Otolaryngology: Most structures of the neck, including the thyroid and parathryoid glands, lymph nodes, and salivary glands, are well-visualized by high-frequency ultrasound with exceptional anatomic detail. Ultrasound is the preferred imaging modality for thyroid tumors and lesions, and ultrasonography is critical in the evaluation, preoperative planning, and postoperative surveillance of patients with thyroid cancer. Many other benign and malignant conditions in the head and neck can be evaluated and managed with the help of diagnostic ultrasound and ultrasound-guided procedures.
g. Neonatology: for basic assessment of intracerebral structural abnormalities, bleeds, ventriculomegaly or hydrocephalus and anoxic insults (Periventricular leukomalacia). The ultrasound can be performed through the soft spots in the skull of a newborn infant (Fontanelle) until these completely close at about 1 year of age and form a virtually impenetrable acoustic barrier for the ultrasound. The most common site for cranial ultrasound is the anterior fontanelle. The smaller the fontanelle, the poorer the quality of the picture.
h. Neurology: for assessing blood flow and stenoses in the carotid arteries (Carotid ultrasonography) and the big intracerebral arteries
i. Obstetrics: Obstetrical sonography is commonly used during pregnancy to check on the development of the fetus.
j. Ophthalmology: Ultrasound images of the eyes, also known as ocular ultrasonography
k. Pulmonology: Endobronchial Ultrasound (EBUS) probes are applied to standard flexible endoscopic probes and used by pulmonologists to allow for direct visualization of endobronchial lesions and lymph nodes prior to transbronchial needle aspiration. Among its many uses, EBUS aids in lung cancer staging by allowing for lymph node sampling without the need for major surgery
l. Urology: To determine, for example, the amount of fluid retained in a patient's bladder. In a pelvic sonogram, organs of the pelvic region are imaged. This includes the uterus and ovaries or urinary bladder. Males are sometimes given a pelvic sonogram to check on the health of their bladder, the prostate, or their testicles (for example to distinguish epididymitis from testicular torsion). In young males, it is used to distinguish more benign testicular masses (varicocele or hydrocele) from testicular cancer, which is highly curable but which must be treated to preserve health and fertility. There are two methods of performing a pelvic sonography—externally or internally. The internal pelvic sonogram is performed either transvaginally (in a woman) or transrectally (in a man). Sonographic imaging of the pelvic floor can produce important diagnostic information regarding the precise relationship of abnormal structures with other pelvic organs and it represents a useful hint to treat patients with symptoms related to pelvic prolapse, double incontinence and obstructed defecation. It is used to diagnose and, at higher frequencies, to treat (break up) kidney stones or kidney crystals (nephrolithiasis).
m. Musculoskeletal: Tendons, muscles, nerves, ligaments, soft tissue masses, and bone surfaces.
n. Cardiovascular system: To assess patency and possible obstruction of arteries Arterial sonography, diagnose deep vein thrombosis (Thrombosonography) and determine extent and severity of venous insufficiency (venosonography).

All the above description has been given for the purpose of illustration and is not intended to limit the invention in any way. The invention is meant to cover any device of the type described above, regardless of the type of smart device, such as a smart phone or other digital assistant for which it may be adapted, and regardless of any changes in the shape of the ultrasonic array or of the base itself and/or any form of wire or wireless communication in any protocol form.

The invention claimed is:

1. A base for an ultrasonic system that can be easily operated by a patient, the base comprising a cavity and connection elements, adapted to accept and position a smart device and to mechanically and electrically connect the smart device to the base and an ultrasonic array, the ultrasonic array comprising at least one transducer element stimulated by high-voltage pulses in the range of $\pm 5$ $V_{PP}$ to $\pm 300$ $V_{PP}$, which causes the at least one transducer element to vibrate, which in turn generates transmitted acoustic waves in the range of 1 MHz to 15 MHz;
   wherein, the smart device is a personal communication device and when the smart device is inserted into the base and mechanically connected to the base, the base and the smart device can be moved as a single unit by the patient to examine, measure, or monitor his/her internal organs;
   the base characterized in that the ultrasonic array is located on the bottom outer surface of the base.

2. The base according to claim 1 wherein the ultrasonic array has one of the following configurations:
   a) a 1D linear array that produces a straight beam that focuses in one axis at different depths and angles and whose divergence increases with angle and depth;
   b) a 2D square array that has steering capability in three dimensions with spherical or single-axis focus;
   c) a 1.5D square or rectangular matrix array that has steering capability and focuses on one axis at different depths and angles;
   d) a 1D annular array that has spherical focusing at different depths;
   e) a 2D segmented annular array that produces an elliptical or spherical beam with steering capability at different depths and angles; and
   f) a 1D circular array that produces an elliptical or spherical beam with steering capabilities.

3. The base according to claim 1, comprising electronics adapted to operate the ultrasonic array and to convey a signal generated thereby to storage elements.

4. The base according to claim 3, wherein the storage elements are provided in at least one of: the smart device; the base; and a location remote from the base.

5. The base according to claim 1, wherein electrical power to activate the ultrasonic array is supplied from one of: a rechargeable battery and a DC to DC converter located in the base; a rechargeable battery and a switching power supply, comprised of a power stage and a control circuit, located in the base; and a battery in the smart device.

6. The base according to claim 3, wherein some or all of the electronics are located in at least one of: the base; the smart device; and on a semiconductor layer produced integrally with the elements that produce ultrasound waves using wafer technology.

7. The base according to claim 1, wherein the elements that produce ultrasound waves are one of: Capacitive Micromachined Ultrasonic Transducers (CMUT), Piezoelectric Micromachined Ultrasonic Transducers (PMUT), Piezo composite Transducers or bulk Piezo elements Transducers.

8. The base according to claim 1, comprising software adapted to enable operation of the ultrasonic array and to display the results of the operation as visible images.

9. A system for ultrasonic imaging that can be easily operated by a patient, the system comprising: a base; a smart device; an ultrasonic array; electronics adapted to operate the ultrasonic array and to convey a signal generated thereby to storage elements; and software adapted to enable operation of the ultrasonic array, to receive signals relating to ultrasonic images, to perform desired operations on the signals and to display the results of the operations as visible images; wherein the base comprises a cavity and connection elements, adapted to accept and position the smart device and to mechanically and electrically connect the smart device to the base and the ultrasonic array comprises at least one transducer element stimulated by high-voltage pulses in the range of $\pm 5$ $V_{PP}$ to $\pm 300$ $V_{PP}$, which causes the at least one transducer element to vibrate, which in turn generates transmitted acoustic waves in the range of 1 MHz to 15 MHz;

wherein, the smart device is a personal communication device and when the smart device is inserted into the base and is mechanically connected to the base, the base and the smart device can be moved as a single unit by the patient to examine, measure, or monitor his/her internal organs;

the system characterized in that the ultrasonic array is located on the bottom outer surface of the base.

10. The system according to claim 9, wherein the ultrasonic array has one of the following configurations:
a) a 1D linear array that produces a straight beam that focuses in one axis at different depths and angles and whose divergence increases with angle and depth;
b) a 2D square array that has steering capability in three dimensions with spherical or single-axis focus;
c) a 1.5D square or rectangular matrix array that has steering capability and focuses on one axis at different depths and angles;
d) a 1D annular array that has spherical focusing at different depths;
e) a 2D segmented annular array that produces an elliptical or spherical beam with steering capability at different depths and angles; and
f) a 1D circular array that produces an elliptical or spherical beam with steering capabilities.

11. The system according to claim 9, wherein data integrity, encryption, and other data activities can be supported from a mobile network operator's servers or a cloud.

12. The system according to claim 9, wherein all digital and analog components of an ultrasound system are located on the base.

13. The system according to claim 9, wherein all digital and analog components of an ultrasound system are implemented in existing chips on the smart device.

14. The system according to claim 9, wherein at least a part of the software adapted to receive signals relating to ultrasonic images and to perform desired operations thereon is located on at least one of: the base and the smart device.

15. The system according to claim 14, wherein the smart device comprises dedicated software, relative to operation of the system, in the form of an application that is downloaded from one of: the internet, a cloud, or from the base.

16. The system according to claim 9 comprising communication components allowing at least one of: two-way communication between the base and the smart device and two-way communication between the system and an external location.

17. The system according to claim 16, wherein at least a part of the communication components are located on at least one of: the base and the smart device.

18. The system according to claim 16, wherein the base has an internal code (characters and numbers) that provides its unique identification; thereby allowing secured communication with remote locations.

19. The system according to claim 18, wherein the secured communication allows a physician to take over the control of the application in the smart device and record, send images or video from the system to his computer, to the cloud or to any other desired location.

20. The system according to claim 18, wherein the secured communication allows a patient using the system to send images or video to a medical center or to a physician.

21. A base for an ultrasonic system that can be easily operated by a patient, the base comprising: an ultrasonic array with at least one transducer element stimulated by high-voltage pulses in the range of $\pm 5$ $V_{PP}$ to $\pm 300$ $V_{PP}$, which causes the at least one transducer element to vibrate, which in turn generates transmitted acoustic waves in the range of 1 MHz to 15 MHz;

a lower section comprising a cavity and connection elements, adapted to accept and position a smart device and to mechanically connect the smart device to the base and to electrically connect the ultrasonic array to the smart device and to electronic components mounted on a "T" shaped PCB that is fitted into the interior of the base; and a planar vertical back wall, which is integral with the lower section;

wherein, the smart device is a personal communication device and when the smart device is inserted into the base and is mechanically connected to the base, the base and the smart device can be moved as a single unit by the patient to examine, measure, or monitor his/her internal organs;

the base characterized in that the ultrasonic array is located on the bottom outer surface of the base.

* * * * *